United States Patent
Mazer et al.

(10) Patent No.: US 6,200,624 B1
(45) Date of Patent: *Mar. 13, 2001

(54) ENTERAL FORMULA OR NUTRITIONAL SUPPLEMENT CONTAINING ARACHIDONIC AND DOCOSAHEXAENOIC ACIDS

(75) Inventors: Terrence Bruce Mazer, Reynoldsburg; Robert Alan Miller, Columbus, both of OH (US); Charles Allan McCombs; Scott Donald Barnicki, both of Kingsport, TN (US); James Cecil Phillips, Plain City, OH (US); Charles Edwan Sumner, Jr., Kingsport, TN (US)

(73) Assignee: Abbott Laboratories, Abbott Park, IL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 08/592,832

(22) Filed: Jan. 26, 1996

(51) Int. Cl.[7] .................................................. A23L 2/00
(52) U.S. Cl. ..................... 426/590; 426/800; 426/801; 426/605; 424/522; 554/114; 554/175
(58) Field of Search .................................. 426/800, 801, 426/590, 605; 554/174, 175; 424/522

(56) References Cited

U.S. PATENT DOCUMENTS

| | | |
|---|---|---|
| 4,104,286 | 8/1978 | Fallis et al. ............. 260/397.25 |
| 4,670,285 | 6/1987 | Clandinin . |

(List continued on next page.)

FOREIGN PATENT DOCUMENTS

| | | |
|---|---|---|
| 2118893 | 3/1994 | (CA) . |
| 2118894 | 3/1994 | (CA) . |
| 0 443 047 | 8/1991 | (EP) . |
| 1559064 | 1/1978 | (GB) . |
| WO 89/11521 | 11/1989 | (WO) . |
| WO 91/03946 | 4/1991 | (WO) . |
| WO 93/20717 * | 10/1993 | (WO) ................................ 426/801 |
| WO 93/21774 * | 11/1993 | (WO) ................................ 426/801 |
| WO 94/27450 * | 12/1994 | (WO) ................................ 426/800 |
| WO 96/00016 | 1/1996 | (WO) . |

OTHER PUBLICATIONS

Patent Abstracts of Japan, vol. 013, No. 423 (C–638), Sep. 20, 1989 & JP 01 160989 A (Nippon Oil & Fats Co., Ltd., Others: 01), Jun. 23, 1989.

Patent Abstracts of Japan, vol. 011, No. 349 (C–456), Nov. 14, 1987 & JP 62 120340 A (Nippon Oil & Fats Co., Ltd.), Jun. 1, 1987.

Lanzani et al., A New Short–Path Distallation System Applied to the Reduction of Cholesterol in Butter and Lard, J. Am. Oil Chem. Soc., 71, (1994) 609–614.

(List continued on next page.)

*Primary Examiner*—Carolyn Paden
(74) *Attorney, Agent, or Firm*—Donald O Nickey; Thomas D. Brainard

(57) ABSTRACT

This invention is directed to the use of triglycerides containing fatty ester moieties that include arachidonic acid (AA) and docosahexaenoic acid (DHA) in enteral nutritionals or nutritional supplements. These triglycerides are derived from lipid mixtures which have high levels of sterols and phosphorous. A preferred embodiment of the invention comprises an infant or enteral nutritional, or nutritional supplement, that comprises a lipid source derived from egg yolk. The lipid source derived from egg yolk is prepared by transesterification or hydrolysis, subjecting the mixture to distillation, and esterification with glycerin to result in a triglyceride containing the desired fatty acids of AA and DHA and little or no sterols and phosphorus.

24 Claims, 2 Drawing Sheets

U.S. PATENT DOCUMENTS

| | | | |
|---|---|---|---|
| 4,692,280 | | 9/1987 | Spinelli et al. ......... 260/420 |
| 4,698,185 | | 10/1987 | Dijkstra et al. ......... 260/403 |
| 4,857,236 | | 8/1989 | Gunther ......... 260/403 |
| 4,871,768 | * | 10/1989 | Bestrean ......... 514/547 |
| 4,952,606 | * | 8/1990 | Babayan ......... 514/557 |
| 5,013,569 | * | 5/1991 | Rubin ......... 426/801 |
| 5,066,500 | * | 11/1991 | Gil ......... 426/72 |
| 5,084,215 | | 1/1992 | Kearns et al. ......... 260/403 |
| 5,091,117 | | 2/1992 | Athnasios et al. ......... 260/428 |
| 5,106,542 | | 4/1992 | Traitler et al. ......... 554/186 |
| 5,112,956 | | 5/1992 | Tang et al. ......... 530/424 |
| 5,130,061 | | 7/1992 | Cornieri et al. ......... 554/167 |
| 5,223,285 | * | 6/1993 | DeMichele ......... 426/801 |
| 5,250,719 | | 10/1993 | Tronconi ......... 558/146 |
| 5,304,545 | | 4/1994 | Mentink et al. ......... 554/212 |
| 5,308,832 | * | 5/1994 | Garlib ......... 426/800 |
| 5,340,594 | * | 8/1994 | Barclay ......... 426/601 |
| 5,340,603 | * | 8/1994 | Neylan ......... 426/801 |
| 5,342,633 | | 8/1994 | Cully . |
| 5,397,591 | * | 3/1995 | Kyle ......... 426/801 |
| 5,411,751 | * | 5/1995 | Cressenger ......... 426/801 |
| 5,514,656 | * | 5/1996 | Cope ......... 426/656 |
| 5,547,927 | * | 8/1996 | Cope ......... 426/656 |
| 5,661,180 | * | 8/1997 | DeMichele ......... 514/547 |
| 5,883,273 | * | 3/1999 | Miller ......... 554/169 |

OTHER PUBLICATIONS

Abstract of JP 62198351 of Sep. 2, 1987 to Morinaga Milk Ind. Co. Ltd.

Abstract of JP 01160989 (application) of Jun. 23, 1989 to NIOF.

Abstract of Han'guk Ch'uksan Hakhoechi, 1991, 33(8), 602–6 by Han, C.K., et al.

Sim et al., Egg Uses and Processing Technologies New Developments, CAB International, pp. 115–127 (1994).

Abstract of JP 1131189 of May 24, 1989 to Nippon Oils & Fats KK.

Abstract of JP 1051091 of Feb. 27, 1989 to Nippon Oils & Fats KK.

Abstract of JP 62120340 of Jun. 1, 1987 to Nippon Oils & Fats KK.

Abstract of JP 62093294 of Apr. 28, 1987 to Hokuren Nogyo Kyodo.

Abstract of JP 60061520 of Apr. 9, 1985 to QP Corp.

Abstract of JP 71042186 of 00000 to Taiyo Food KK.

Abstract of SU 1701737 of Dec. 30, 1991 to Kompleks Poultry Ind. Res. Prodn. Assoc.

Banerjee, et al., Enrichment of saturated fatty acid containing phospholipids in sheep brain serotonin receptor preparations: use of microwave irradiation for rapid transesterification of phospholipids, Biochimica et Biophysica Acta., 1110(1992) 65–74.

* cited by examiner

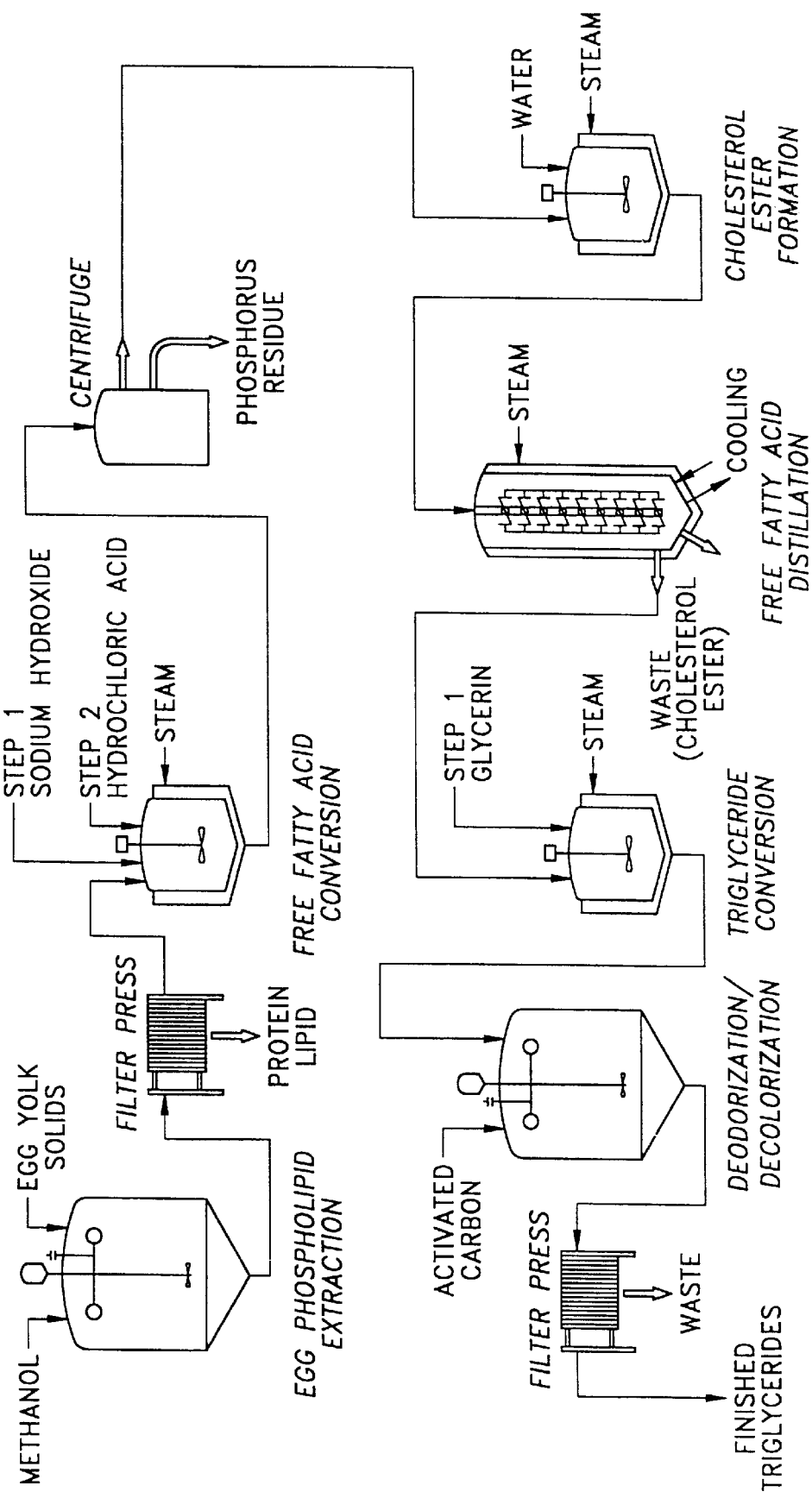

ENTERAL FORMULA OR NUTRITIONAL SUPPLEMENT CONTAINING ARACHIDONIC AND DOCOSAHEXAENOIC ACIDS

FIELD OF THE INVENTION

This invention relates to an enteral nutritional formula and nutritional supplement containing triglycerides prepared by the process disclosed in this invention. The enteral formula can be used as an infant formula or as an adult nutritional. The invention also relates to nutritional supplements which contain arachidonic acid and other long-chain polyunsaturated fatty acids, such as maternal supplements.

BACKGROUND OF THE INVENTION

The composition of human milk serves as a valuable reference for improving infant formula. Much effort has been directed at producing a milk based infant formula which is similar to human milk.

One component of human milk that is receiving more investigation is the fat composition. Human milk fat contains long chain polyunsaturated fatty acids which may play a role in infant development. Many infant formulas do not contain lipids having long chain polyunsaturated fatty acids such as arachidonic acid (C20:4w6) (also referred to herein as AA), ecosapentaenoic acid (also referred to herein as EPA), and docosahexaenoic acid (C22:6w3) (also referred to herein as DHA). Acceptable ingredient sources for these fatty acids are limited, thus the lack of such acids in infant formula and adult nutritionals.

Polyunsaturated acids, in particular the longer chain acids such as AA, DHA, and EPA are natural constituents of many foodstuffs. However these acids are either intimately combined with undesirable components such as cholesterol, phosphorus compounds, or are unsuitable for food applications in their functional form.

The n-6 family of polyunsaturated fatty acids, based on the parent linoleic acid and higher derivatives such as AA, have long been established as essential in human and animal nutrition. More recently, evidence has accumulated for the nutritional importance of the n-3 family of polyunsaturated fatty acids, based on the parent linolenic acid and higher derivatives such as ecosapentaenoic acid (EPA) and docosahexaenoic acid (DHA). These polyunsaturated acids are the precursors for prostaglandins and eicosanoids, a powerful group of compounds which produce diverse physiological actions at low concentrations. The prostaglandins are known to influence blood clotting, inflammatory and anti-inflammatory response, cholesterol absorption, bronchial function, hypertension, visual acuity and brain development in infants, and gastric secretions, among other effects.

Egg yolk lipids contain AA (arachidonic acid) and DHA (docosahexaenoic acid) and are widely consumed in diets of both children and adults. Lipids isolated from egg yolks could be deemed unacceptable for use in infant formula due to high levels of cholesterol which suffers from negative public opinion, and the troublesome levels of phosphorus. The AA and DHA are present in egg yolk lipids primarily as phospholipids. Thus, infant formulas fortified with egg yolk lipids exhibit levels of cholesterol and phospholipids which far exceed the level of such nutrients found in breast milk.

Typically, the amount of lipids in egg yolk is about 65% by weight (wt %) of the dry matter. In such lipids, about 66 wt % of the lipid is triglycerides, of which about 30 wt % is phospholipids, and about 4 wt % is cholesterol. The phosphorus content of the lipids is about 1 wt % to 2 wt %.

Several commercial egg lipid ingredients are presently available. The first, OVOTHIN 120, is a total egg yolk lipid extract supplied by Lucas Meyer of 765 East Pythian Ave., Decatur, Ill. 62526. OVOTHIN 120 contains triglyceride, phospholipid and cholesterol. A second ingredient, supplied by Psanstiehl Laboratories, Inc. of 1219 Glen Rock Ave., Waukegan, Ill. 60085 is an egg yolk extract which is 90% phospholipids. Also, purified egg phospholipid is available from Genzyme Corporation of One Kendill Square, Cambridge, Mass. 02139. Unfortunately, all the above ingredients negatively impact the phosphorus levels of infant formula when used at the proper fortification level to achieve AA and DHA target levels approximating the content of AA and DHA in human milk. The proper fortification would require that about 7–9 wt % of the fat in the infant formula be composed of phospholipid. Human milk fat contains 1–3 wt % phospholipid. Furthermore, the use of OVOTHIN 120 increases cholesterol in infant formula above the levels found in human milk.

There are numerous methods in the literature for recovering phospholipids from lipid mixtures. For example, U.S. Pat. No. 4,698,185 discloses a method of separating phospholipids from crude vegetable triglyceride mixtures. The method involves the addition of water in a mass ratio about equal to the mass of phospholipids present in the lipid mixture, with or without heating, and with or without co-addition of citric or phosphoric acid, to cause the phospholipids to hydrate and separate into a second phase.

Such degumming methods, however, were designed for the removal of 1 to 2 weight percent of phospholipids from crude vegetable triglycerides and are not directly applicable to the purification of other natural lipid mixtures, such as egg yolk lipids because of the higher levels of phospholipids (30–40 wt %) in egg yolk lipids. Addition of a 1:1 mass ratio of water to phospholipid with large amounts of phospholipids present causes the formation of a stable emulsion which prevents phase separation. Moreover, sterols tend to partition between both the phospholipid and triglyceride phases.

It is desirable to provide a process by which cholesterol and other sterol compounds (many of which can be metabolized to cholesterol or its derivatives) can be extracted from various foodstuffs, thereby producing low-cholesterol versions of such foodstuffs. However, the process must not introduce into the foodstuff any material which is not generally recognized as safe for use in foodstuffs. In addition, the process should remove from the foodstuff not only cholesterol itself but also cholesterol derivatives and other sterol compounds which can be metabolized in the body to cholesterol or derivatives thereof, and which thus affect cholesterol levels in the body. Furthermore, the process should leave the foodstuff in a form which is as close as possible to that of the original, high cholesterol foodstuff. Finally, the cholesterol-removal process should not remove vitamins and other important nutrients of the foodstuff.

Numerous attempts have previously been made to provide a cholesterol-removal process which meets these exacting criteria. U.S. Pat. No. 4,692,280, discloses a process for the purification of fish oils in which the oil is extracted with supercritical carbon dioxide to remove cholesterol, together with odoriferous and volatile impurities. Such carbon dioxide extraction processes, however, suffer from the disadvantage that they must be operated under pressure to keep the carbon dioxide in the supercritical phase, which increases the cost of the apparatus required. In addition, such carbon dioxide extraction processes are not very selective in the removal of cholesterol, and thus remove valuable constituents of the foodstuff. In addition, the properties of some foodstuffs may be altered disadvantageously by contact with supercritical carbon dioxide; for example, in some cases the carbon dioxide removes flavoring and odoriferous components which affect the taste and smell of the treated foodstuff.

U.S. Pat. No. 5,091,117 discloses a process for removing at least one sterol compound and at least one saturated fatty acid from a fluid mixture by contacting the fluid mixture with an activated charcoal. U.S. Pat. No. 5,091,117 states however, in column 12, lines 4–19, that the process should not be used for removing cholesterol from materials, such as egg yolks which contain a combination of cholesterol and proteins, since a significant adsorption of proteins and their constituent amino acids occurs on the charcoal.

British Pat. No. 1,559,064 discloses a process for removing cholesterol from butter triglycerides by distillation. However, Lanzani et al [J. Am. Oil Chem. Soc. 71, (1994) 609] determined that only 90% of the cholesterol could be removed using the process disclosed in British Pat. No. 1,559,064 without seriously affecting the quality of the end product. Excessive time at the high temperatures needed for more complete cholesterol removal was found to cause cis-trans isomerization of the polyunsaturated fatty acids. The trans form of polyunsaturated fatty acids are considered undesirable in food products.

Egg yolk is an example of a lipid mixture rich in polyunsaturated fatty acids including AA and (all-cis)-4,7,10,13, 16,19-docosahexaenoic acid (DHA) in which the polyunsaturated fatty acids are predominantly bound in the phospholipids and which contain high levels of cholesterol. It is desirable to provide a process for the manufacture of egg-derived fatty acids and fatty acid esters high in polyunsaturated fatty acids which removes cholesterol and phosphorus residues without degrading or causing cis-trans isomerization of the essential polyunsaturated fatty acids contained therein or the taste and flavor of foods prepared using such fatty acid and ester mixtures. Moreover, the process for the manufacture of the fatty acid and ester mixtures should use materials which are on the Generally Recognized As Safe (GRAS) list of the U.S. Food and Drug Administration in order for the final product to be used in foods.

U.S. Pat. No. 4,670,285 to M. Clandinin of Jun. 2, 1987 discloses the use of lipid extracted from egg yolk in infant formula. The lipids of the Clandinin reference include polyunsaturated lipids found in human milk such as C:20 or C:22 w6 and C:20 or C22 w3 fatty acids. The lipids of Clandinin contain the unacceptable levels of cholesterol and phosphorus of the original egg yolk material.

Abstract of JP 62198351 of Sep. 2, 1987 to Morinaga Milk discloses a substitute mothers' milk composition which contains egg yolk lipid extracted from egg yolk with ethanol. The lipid is preferably combined so that a 100 g milk composition contains 68 mg of cholesterol. However, the 68 mg of cholesterol translates to about 680 mg/L (liter) or greater than four times that found in average composition human milk.

U.S. Pat. No. 5,112,956 of May 12, 1992 to P. Tang, et al. discloses a method for the removal of lipids and cholesterol from protein material such as that in egg yolk by treating the protein with an extraction mixture comprising a lower alcohol, water, and an acid in concentrations selected to extract cholesterol and lipids from the protein. The preferred lower alcohol of this reference is ethanol and a primary object is obtaining protein suitable for human consumption.

PTC publication WO 89/11521 of Nov. 30, 1989 discloses a process for preparing EPA and DHA and their esters from oils of animal and/or vegetable origin by subjecting the raw oil to alkaline hydrolysis, acidifying the soap so formed with a mineral acid in aqueous solution, extracting the resulting mixture with petroleum ether and after washing and concentration, the combined extracts are submitted to one or more distillation steps with the pressure and temperature parameters being suitably changed in order to obtain a whole range of desired products.

Abstract of JP 1160989 (application) of Jun. 23, 1989 to NIOF. Fresh fish eggs are extracted with solvent of distilled water, methanol/chloroform, acetone, ether, under oxygen-free conditions to extract lipids and eventually isolate a docosahexaenoic acid- containing phosphatidylcholine.

Abstract of Han'guk Ch'uksan Hakhoechi, 1991, 33(8), 602–6 by Han, C. K., et al. Egg yolk was ground with trichloromethane and methanol. Lipid extract was converted to methyl esters by transesterification with boron trifluoride and methanol. The methyl esters were analyzed for various fatty acids. C20–22 polyunsaturated acids accounted for 4.3% of the total.

In the present invention, egg yolk derived glyceride compositions, also simply referred to herein as Processed Natural Ingredients, are prepared which typically contain about 4 wt % of AA and about 1.5 wt % of DHA based on the weight of the Processed Natural Ingredients and wherein the amount of phosphorus can be reduced to less than about 0.002 wt % (20 ppm) and the amount of cholesterol reduced to less than about 0.1 wt % of the processed Natural Ingredients. Preferably at least 95% and particularly at least 98% of the cholesterol and other sterols, and phosphorus compounds are removed from the lipid mixture staring material, e.g. egg yolks in the process of this invention, and such highly purified fatty acids or esters thereof are referred to herein as being "essentially free of cholesterol, sterols and phosphorus compounds". The Processed Natural Ingredients can be that of mono-, di-, or triglycerides as well as mixtures thereof.

Unless the context indicates otherwise, the following terms shall have the following meaning:

"AA" is arachidonic acid (C20:4w6);

"alkaline metal" is an alkaline earth metal or alkali metal such as calcium, magnesium, sodium, or potassium;

"DHA" is docosahexaenoic acid (C22:6w3);

"egg derived triglycerides" are one of the Processed Natural Ingredients (as defined below) wherein a major portion, preferably at least 75% by weight of the glycerides and particularly at least 90% of the glycerides are triglycerides derived from egg yolk;

"ester route" is the process which comprises the preparation of fatty acid esters by transesterifying fatty acids of lipids to lower alkyl esters of the fatty acids;

"essentially free of cholesterol, sterols, and phosphorus compounds" means that at least 95%, preferably at least 98%, of the cholesterol and other sterols, and phosphorus compounds are removed from a lipid starting material by the process of the present invention;

"FAP" is fatty acid profile;

"FAME" is fatty acid methyl esters;

"free fatty acid route" is the process which comprises the production of free fatty acids and/or esters thereof by hydrolysis of naturally occurring lipids to free fatty acids;

"GC" is gas chromatography;

"lower alkane" is an alkane having from 1 to 4 carbon atoms;

"lower alkyl" is an alkyl having from 1 to 4 carbon atoms;

"lower alkanol" is a monohydric alcohol having from 1 to 4 carbon atoms;

"lower alkoxide" is an alkyl oxide group having from 1 to 4 carbon atoms such as in sodium methoxide;

"mL" means milliliter;

"N/AP" means not applicable;

"N/D" means not detectable;

"N/R" means not reported; and

"Processed Natural Ingredients" are the compositions containing glycerides prepared by reacting glycerol with the free fatty acids or lower alkyl esters thereof in the process of this invention;

"TLC" is thin layer chromatography.

BRIEF DESCRIPTION OF THE DRAWINGS

FIG. 2 is a schematic flow diagram entitled "FREE FATTY ACID ROUTE FOR EGG PHOSPHOLIPID TO TRIGLYCERIDE CONVERSION" and shows important steps of a preferred method for making the triglyceride composition of the Processed Natural Ingredients by use of methanol as the extraction solvent for lipids from egg yolk solids by the free fatty acid route.

DISCLOSURE OF THE INVENTION

Figure 1:
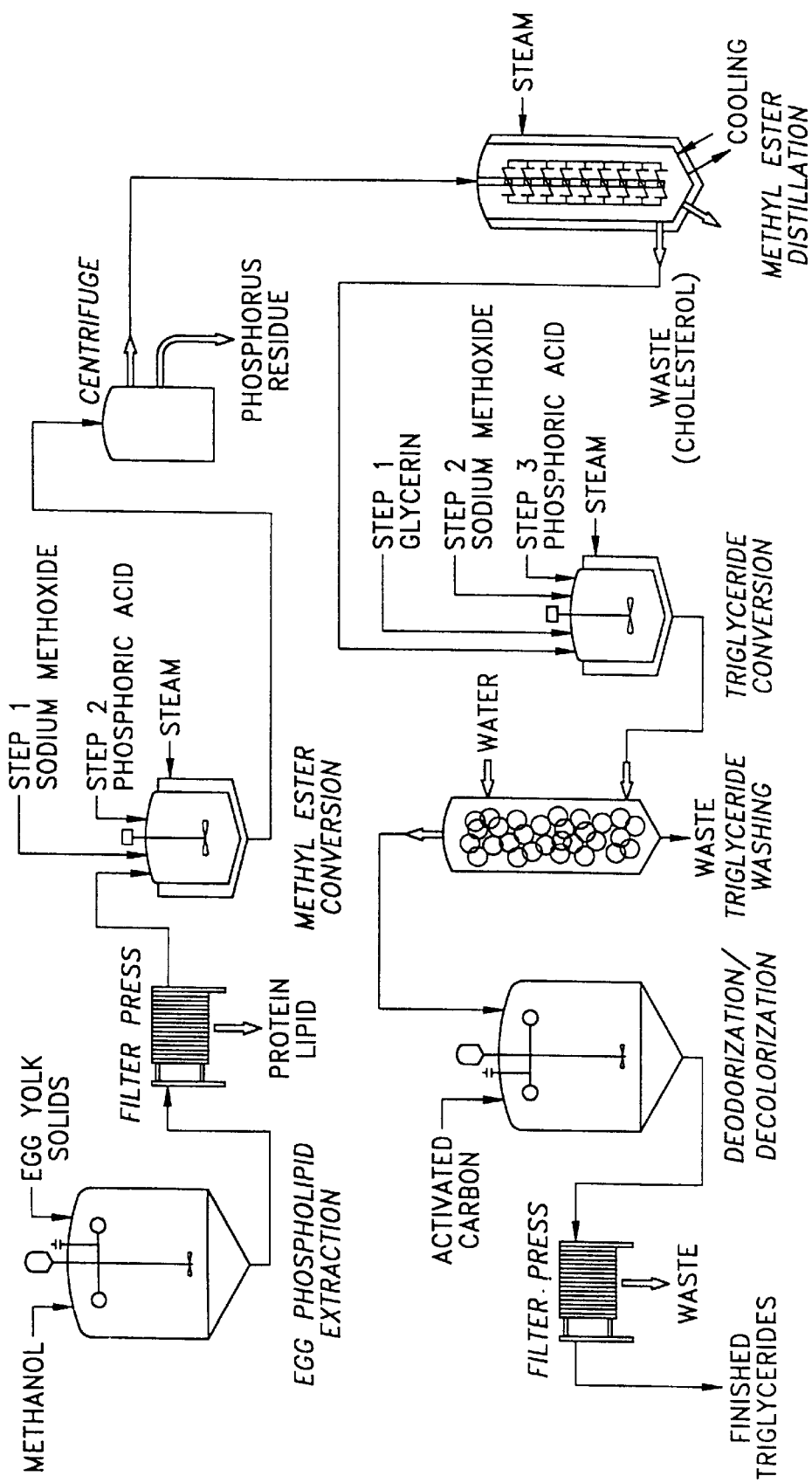
FIG. 1 is a schematic flow diagram entitled "ESTER ROUTE FOR EGG PHOSPHOLIPID TO TRIGLYCERIDE CONVERSION" and shows important steps of a preferred method for making the triglyceride composition of the Processed Natural Ingredients by use of methanol as the extraction solvent for lipids from egg yolk solids by the ester route.

The present invention relates to the use of triglycerides in nutritional products or supplements wherein the triglycerides are produced in accordance with a process disclosed herein. The process produces triglycerides which are high in polyunsaturated fatty acids, which are essentially free of cholesterol and other sterols, and phosphorus, and are derived from lipid mixtures such as naturally occurring lipid mixtures. The sterols and the phosphorus compounds are removed without degrading or causing cis-trans isomerization of the essential polyunsaturated fatty acids or esters thereof contained therein or the taste and flavor of foods prepared using such lipids mixtures. Moreover, the process of the present invention uses materials which are on the Generally Recognized As Safe (GRAS) list of the U.S. Food and Drug Administration.

In one aspect of this invention, the process broadly comprises the steps of:

(A) subjecting a lipid mixture containing phospholipids, triglycerides and sterols, including cholesterol, to treatment selected from the group consisting of (1) hydrolysis to form a free fatty acid phase and an aqueous phase comprised of water, glycerol and phosphorus compounds (2) alkaline transesterification with a lower alkanol to produce a lower alkyl fatty acid ester phase comprised of lower alkyl fatty acid esters and sterols and an aqueous phase comprised of water, glycerol and phosphorus compounds;

(B) separating the aqueous phase from (1) fatty acid phase or (2) lower alkyl fatty acid ester phase products formed in Step (A);

(C) distilling the fatty acids or esters thereof of Step (B) at a temperature of at lest 100° C. to separate and recover in the distillate (1) free fatty acids or (2) lower alkyl esters of the fatty acids wherein said fatty acids or esters thereof have reduced concentrations of cholesterol and other sterols, and phosphorus compounds in relation to the lipid mixture; and (D) subjecting the (1) purified free fatty acids or (2) purified lower alkyl esters from Step (C) to treatment selected from the group consisting of: reaction of the purified free fatty acids with a C1 to C10 monohydric or polyhydric alcohol to produce a fatty acid ester, or (2) transesterification of the purified lower alkyl ester obtained in Step (C) with a C1–C10 monohydric or polyhydric alcohol to produce a fatty acid ester of said C1–C10 alcohol wherein said alcohol has a different number of carbon atoms from that used in the transesterification of Step (A)

The selection of the specific steps in the chemical synthesis method of this invention compliment each other so as to arrive at the Processed Natural Ingredients in an economic and efficient manner useful in the manufacture of enteral formulas.

In another aspect of the invention, phospholipids having a high concentration of AA are prepared by contacting a natural lipid source, e.g., egg yolk and preferably egg yolk solids, with a solvent consisting essentially of methanol at a temperature of about 20° C. to 68° C.

In another aspect of the invention a lower alkanol is included with the lipid mixture to assist or cause the mixture to separate into a top phase comprising phospholipids, sterols and alcohol and a bottom phase comprising triglycerides and sterols. The top phase is then used for subsequent processing.

In yet another aspect of the invention, which comprises the free fatty acid route, the process comprises the steps of:

(A) hydrolyzing a lipid mixture containing phospholipids, triglycerides, and sterols to form a two-phase product containing a fatty acid phase comprising free fatty acids and sterols, and an aqueous phase comprising water, glycerol, and glycerol phosphoric acid esters;

(B) separating the aqueous phase from the fatty acid phase of the two-phase product formed in Step (A);

(C) reacting the fatty acids with the sterols in the fatty acid phase from Step (B) at a temperature of 150° C. to 250° C. to form a mixture comprising sterol fatty acid esters and water; and (D) distilling the sterol fatty acid esters formed in Step (C) at a temperature of 130° C. to 250° C. and a pressure of $1 \times 10^{-3}$ kPa to 0.5333 kPa, to recover purified fatty acids which are essentially free of cholesterol, sterols, and phosphorus compounds; and optionally;

(E) reacting the purified fatty acids prepared in Step (D) with a monohydric or polyhydric alcohol in a molar ratio of 1 to 2 moles of fatty acid to each hydroxy equivalent of the alcohol to produce a fatty acid ester.

In still another aspect of the invention the egg yolk is extracted with a lower alkyl alcohol and the subsequent processing follows the same steps as for that described above for the ester route or the fatty acid route wherein the egg yolk lipid was the starting material. The use of methanol to extract lipids is advantageous, particularly at temperatures from about 20° C. to the boiling point of methanol, i.e., 68 degrees C., since the amount of AA extracted is unexpectedly greater in comparison with the use of other alkanols such as ethanol or propanol. Additionally, methanol is a solvent accepted for use in preparation of food ingredients.

In a further aspect of the invention purified free fatty acids, lower alkyl esters of the fatty acids, or mixtures thereof are recovered from the distillation step without proceeding to the esterification step.

Still further aspects of the invention include fractionation techniques for concentrating fatty acids such as AA and DHA.

A further aspect of the invention is directed to liquid or powdered enteral formulas such as an enteral formula comprising: from about 10 to 35 grams of protein per liter of formula; carbohydrates, which may include those of dietary fiber of between 60 and 110 grams per liter of formula; and from about 20 to 45 grams of fat per liter of formula wherein the fat includes the egg derived triglycerides in sufficient amount to provide triglycerides having ester groups containing from about 0.1 wt % to 2.0 wt % and preferably about 0.1 to 1 wt % (weight percent) of AA based on the total fat in the enteral formula and about 0.05 wt % to 0.5 wt % of DHA based on total fat in the formula and wherein the said egg derived triglyceride contains less than 1%, 0.1% preferably less than and more preferably less than 0.05% phosphorus and less than 1% and preferably less than 0.5% cholesterol by weight based on the weight of the egg derived triglycerides. The enteral formula, in a simple form, contains a nutritionally adequate source of amino nitrogen, carbohydrates and edible fats together with the egg derived triglycerides. There is also disclosed enteral formulas wherein the AA and DHA are prepared by the method disclosed herein. Methods for manufacture of AA and DHA containing enteral formula is still another aspect of the invention.

A number of techniques were unsuccessfully tried to obtain glycerides of AA and DHA in an economic and practicable manner which would be suitable for use in an enteral formula such as infant formula. One of the unsuccessful techniques was thermal cracking. When egg yolk lipids and water were mixed and heated, there was a severe foaming problem. When water was limited to one equivalent based on phospholipid, foaming could be controlled. After 5 minutes at 250° C. with no solvent, TLC (thin layer chromatography) showed a mixture of triglyceride and diglyceride and starting material (phospholipid). However, the reaction mixture was very dark in color and non-homogeneous. The dark color was indicative of decomposition. Lowering the temperature to 200° C. for 30 minutes showed no obvious benefits.

Still another advantage of this invention is the finding that temperatures of up to about 250 degrees C. can be used in some of the method steps without decomposition or appreciable darkening of the AA and DHA or methyl esters thereof. This is believed to be unexpected since a test conducted with methyl oleate began to darken at about 75° C.

DETAILED DESCRIPTION OF THE INVENTION

Naturally occurring lipid mixtures high in polyunsaturated fatty acids are derived from animal and vegetable matter. Sources of lipid mixtures include: marine animals such as blue-colored fish, e.g., the mackerel, sardine, mackerel pike and herring; salmon; cod liver oil; animal marine plankton, such as krill and the various shrimp-like copepods; eggs; green leafy vegetables such as spinach, broccoli, and purslane; and oilseeds such as soya, sunflower, flax, canola, rapeseed, and cotton seeds. Any source of lipid mixtures high in polyunsaturated fatty acids may be used in the process of the present invention.

The lipid mixture is separated from the animal or vegetable fat or oil by extraction or leaching with a solvent such as alcohol or hydrocarbon. Illustrative of solvents for leaching or extracting lipids there can be mentioned lower alkanols having from 1 to 4 carbon atoms such as methanol, ethanol, isopropanol, and the like; hydrocarbons such as hexane; ethers such as petroleum ether and diethyl ether; lower alkanes under pressure such as those having from 3 to 4 carbon atoms and halogen substituted lower alkanes such as trichloromethane and dichloromethane; ketones such as acetone; as well as mixtures of the foregoing. For example, egg yolk powder may be mixed with a lower alkanol, e.g., methanol, which yields a lipid mixture containing phospholipids, triglycerides and sterols in liquid form, and solid protein material. The solid protein material is easily separated from the lipid mixture by methods known in the art such as filtration or centrifugation.

The preferred lipid source is egg yolks. The egg yolks used in this invention are generally derived from various avian species such as the hen, turkey, etc. and preferably the hen. However, eggs of other animals can be used, e.g. that of fish such as salmon eggs as well as eggs of turtles.

A typical composition of hen's egg yolks as found in Sim, J. S. et al., Egg Uses and Processing Technologies, page 120 (1994) is as follows on a percent by weight basis:

(a) 47.5% water, 33.0% lipids, 17.4% protein, 0.20% of carbohydrates (free), 1.1% of inorganic elements; and others of 0.8%;

(b) as to lipid composition (from total lipids): triglycerides of 71–73%, cholesterol of 4–6%, phospholipids of 23–25%, lecithin (in phospholipids) of 70–77%, C16–C18 fatty acids 99.5%, saturated fatty acids 44%, monounsaturated fatty acids 44% and polyunsaturated fatty acids of 10.2%. As far as the C16 and C18 fatty acids are concerned in the preceding egg yolk analysis, it does not appear to applicants that the analysis accounted for long chain fatty acids.

Egg yolks can be in different forms such as liquid, frozen, or solid with or without conventional additives such as silica flow agents. Egg yolk solids can be obtained from eggs by various conventional means such as by spray drying egg yolks, freeze drying, etc. Egg yolk solids typically have 5% maximum moisture content, a pH of 6.5±3, a 56.0 wt % minimum fat content, protein of 30 wt % minimum. A preferred form of egg yolk useful in the present invention is egg yolk solids.

The long chain unsaturated fatty acids such as AA and DHA in egg yolk lipids are found predominantly in the phospholipid fraction. In the methanol solution of the egg yolk lipids of this invention, the amount of lipids is typically about 38 wt %; the amount of AA is about 4 wt %; and the amount of DHA is about 1.5 wt % as determined by a relative fatty acid profile. However, the quantity of these lipid components can vary depending on the species of animal, its diet, time of year, etc.

The amount of phosphorus and cholesterol contained in the Processed Natural Ingredients is very low. Generally, the quantity of phosphorus can vary from about 0.1 wt % to 0.0001 wt % based on the Processed Natural Ingredients. It is preferred that the quantity of phosphorus be less than 0.1 wt % and particularly less than 0.01 wt % of the Processed Natural Ingredients. It is preferred that the quantity of cholesterol be less than 0.5 wt % and particularly less than 0.1 wt % based on the weight of the Processed Natural Ingredients. The distilled free fatty acids as well as the distilled lower alkyl esters of this invention will also have the low phosphorus and low cholesterol levels give above for the Processed Natural Ingredients. It is particularly preferred that the fatty acid and ester products of this invention be essentially free of cholesterol, sterols and phosphorus compounds.

The quantity of organic solvent used for extracting lipids from a lipid source, can vary over a broad range sufficient to dissolve the lipids. In the case of egg yolk solids, such quantity can vary from about 40 ml to over 800 ml of methanol based on 100 grams (g) of egg yolk solids. Larger quantities of methanol can be used but such larger quantities serve little useful purpose since it needs to be removed in later steps of the process.

As can be seen in Example 4 herein the use of methanol to extract lipids from egg yolk provides an unexpected high concentration of AA in the egg lipid extract in the temperature range of about 20° C. to 68° C. and preferably 30° C. to 65° C.

By extracting egg yolk with methanol, a phospholipid-rich egg lipid extract is obtained. It is the phospholipids which contain most of the AA and DHA of the egg yolk. When a solvent other than methanol is used for extracting the lipids, the extraction temperature can vary from about 0° C. to the boiling point of the solvent. The quantity of such other organic solvent can be the same as in the use of methanol.

The addition of a lower alkanol as used in the extraction of lipids from a lipid source or when simply added to a lipid mixture from which the triglycerides have not been separated from the phospholipids before hydrolysis or transesterification causes the formation of two liquid phases when the temperature is maintained between 20° C. and 68° C., preferably 30° C. to 65° C. The top phase is comprised of phospholipids, sterols, and alcohol, the bottom phase is comprised of triglycerides and sterols. The triglyceride phase is removed by methods known in the art such as decantation. For lipid mixtures such as egg yolks in which the polyunsaturated fatty acids such as AA, DHA and EPA are predominantly bound in the phospholipids rather than the triglycerides, the addition of the alcohol is convenient and inexpensive method of removing the triglycerides and concentrating the polyunsaturated fatty acids in the remaining lipid mixture. The addition of the lower alkanol does not interfere with the subsequent hydrolysis reaction nor the transesterification reaction and can provide the lower alkanol needed for transesterification of the fatty acid portion of the phospholipid. In case methanol is used as the lower alkanol for the phase separation, the methanol is preferably added in a mass ratio of about 0.5 to 1 to 3 to 1 alcohol to the source of the lipids, e.g., egg yolk solids. The addition of methanol outside this range either does not result in the formation of a two phase mixture or results in poor partitioning of triglycerides and phospholipids into their respective phases. Water can be used to assist in such separation and the quantity of water can vary over a wide range such as that of from about 1 wt % to about 100 wt % based on the source of the lipids, e.g., egg yolk solids.

A brief description of a preferred embodiment of the invention involving the ester route is as follows. Lipids are extracted from a lipid source, e.g., egg yolk solids, with methanol; the lipids are separated from proteins and other insoluble constituents of the lipid source; the methanolic solution of lipids is submitted to alkaline transesterification and subsequent neutralization to convert the fatty acids of lipid glycerides into fatty acid methyl esters wherein the reaction medium also contains sterols such as cholesterol as well as glycerine, phosphorus, and other products in the lipids or resulting from the transesterification and subsequent neutralization; the methyl esters and sterols of the foregoing are separated, such as by precipitation or phase separation, from an aqueous phase which includes phosphorus from the lipids, principally from phospholipids, as well as glycerine and some of the methanol; the methyl esters are distilled to separate sterols from the methyl esters; and the methyl esters are subjected to esterification, specifically transesterification, in the presence of glycerol and subsequent neutralization or quenching of the reaction product to produce the egg derived triglycerides of fatty acids from the egg yolk lipids wherein such triglycerides have a high concentration of AA and DHA ester groups and wherein such egg derived triglycerides contain reduced quantities of cholesterol and phosphorus.

After the lipids are dissolved in the methanol or other organic solvent, the insoluble egg yolk components such as protein are separated from the methanolic solution of lipids. This can be done by various conventional techniques such as the use of a filter press, centrifuging, vacuum filtration, etc.

In the case of egg yolk is extracted with methanol, the extract is preferably separated into a triglyceride phase and a phospholipid phase by the addition of water and centrifuging. Analysis of a sample with methanol as the solvent for extracting the lipids showed that the triglyceride phase had no detectable phosphorus and was low in cholesterol. A fatty acid distribution assay of such sample showed that the triglyceride phase contained only 0.37% AA and 0.13% DHA. This demonstrates that the phospholipids were cleanly separated from the triglyceride fraction. With the separation and isolation of the phospholipid phase, a large percentage of triglyceride can be removed and final products such as the purified free fatty acids, lower alkyl fatty acid esters and Processed Natural Ingredients can be prepared with a higher concentration of the polyunsaturated acids such as DHA and AA.

Although separation of phospholipids from triglycerides as described above prior to hydrolysis or transesterification is advantageous, it was found that the majority of cholesterol also separated into the phospholipid layer. Thus, an effective method for removing the cholesterol and other sterols from this or subsequent reaction mixtures needs to be used.

In the ester route, after removal of insoluble material from the lipid source, the solution of lipids, preferably phospholipids such as those separated from egg yolk triglycerides, are then ready for transesterification with a lower alkanol and a catalytic quantity of an alkaline metal lower alkoxide. In case the lipid is not dissolved in a lower alkanol, such alkanol needs to be added for the transesterification. Lipid solvents other than lower alkanols should preferably be removed at this step. At this stage neutralization might be required because egg yolk lipids are typically slightly acidic. The alkaline metal portion of the alkoxide of the transesterification catalyst can be that of an alkaline earth metal or alkali metal such as calcium, magnesium, sodium or potassium. Preferred alkaline metals are those of sodium or potassium and particularly that of sodium. The lower alkyl oxide, i.e., the alkoxide, can have from 1 to 4 carbon atoms and preferably from one to 2 carbon atoms, e.g., methyl, ethyl, propyl, isopropyl, butyl, isobutyl, etc. Illustrative of the alkaline metal lower alkoxides there can be mentioned those of sodium methoxide, sodium ethoxide, sodium n-propoxide, potassium methoxide, potassium ethoxide, and the like.

The quantity of the alkaline metal lower alkoxide catalyst can vary over a wide range sufficient to neutralize the lower alkanol solution of lipids as well as providing a catalytic amount for effecting the transesterification of the lipids in the lower alkanol to the corresponding lower alkyl esters of the fatty acids in the lipids. Alternatively, the acidity in the alcoholic solution of lipids can be neutralized with other basic materials such as calcium oxide and then an alkaline metal lower alkoxide is used in a catalytic amount, e.g., about 0.4 wt % of sodium methoxide based on the weight of lipid.

The temperature for the transesterification of lipid to lower alkyl esters of the fatty acids such as that of AA or DHA can vary over a broad range such as that of about 20° C. to the boiling point of the lower alkanol, e.g., 68° C. in the case of methanol, and preferably at a temperature of about 50° C. to the boiling point of the lower alkanol.

After the transesterification of lipids to the lower alkyl esters of the corresponding fatty acids, the reaction medium is preferably neutralized with an acid, as is conventional with transesterification reactions. However, such neutralization is not necessary. Illustrative of acids which can be employed are inorganic acids such as phosphoric, hydrochloric, sulfuric, etc. as well as organic acids such as acetic, and the like.

Transesterification of the lipids produces an aqueous phase containing phosphorus compounds, generally as precipitates, and lower alkanol and glycerine. There is also produced a lower alkyl ester phase which contains the fatty acid esters and sterols such as cholesterol. The aqueous phase material including precipitates is separated from the phase containing the lower alkyl esters of the fatty acids and the cholesterol. The precipitate is preferably separated by filtration or by centrifuging whereas liquid materials can be separated by means such as decanting, or centrifuging. Although much of the lower alkanol is removed at this stage, about 5 wt % to 10 wt % of the crude lower alkyl ester fraction is lower alkanol. The lower alkanol can be removed by evaporative means. Thus, after neutralization of the transesterification reaction, two distinct layers will form (i.e., phase separation). The upper layer is principally crude lower alkyl esters of the fatty acids, however, it contains some quantity of lower alkanol such as about 2 to 20%. The lower alkanol is removed by evaporation or distillation prior to the distillation of the alkyl esters of the egg yolk fatty acids. Once the above two phases are separated, the lower layer, principally dark (brownish) in color, contains a majority of the alkanol. Upon extended standing or removal of some alkanol, additional amounts of crude lower alkyl esters can be isolated, thus increasing the effective yield.

The crude lower alkyl esters of the fatty acids are then separated from the cholesterol by distillation under reduced pressure such as with a molecular or short path still. Since unsaturated fatty acids such as AA and DHA are sensitive to temperature in that they degrade, particularly in formation of trans isomers, the distillation is preferably conducted at a temperature of 100° C. to about 250° C. The distillation equipment is preferably of the type which permits distillation at low temperature and reduced pressure such as in the use of molecular distillation or short path distillation. Preferably, the distillation is conducted at a temperature of 130° C. to 230° C. The pressure can vary from about $1\times10^{-3}$ kPa to 0.533 kPa to recover the purified lower alkyl esters of the fatty acids from the distillation.

After distillation of the lower alkyl esters of the fatty acids, such esters are then converted to oter esters, e.g., glycerides by transesterification, with the removal of lower alkanol, preferably in the presence of catalytic quantities of an alkaline metal lower alkyl oxide.

The purified (distilled) lower alkyl esters of the fatty acids which are transesterified with a monohydric or polyhydric alcohol are generally in a molar ratio of 1 to 2 moles of the lower alkyl ester of the fatty acid to each hydroxyl equivalent of the alcohol in the transeterification reaction. In order to minimize formation of mono- and diglycerides in the preparation of triglycerides, it is preferred that the quantity of glycerol in the preparation of the egg derived triglycerides be no more than about 95% of the stoichiometric quantity required for formation of the triglycerides.

The temperature used for the transesterification reaction of the lower alkyl esters of the fatty acids should be no higher than about 250° C. and preferably no higher than 200° C. since the double bonds in the polyunsaturated fatty acids are heat labile and can be converted from cis to trans isomers. Thus the temperature of the transesterification can vary over a wide range such as that of from about 75 to 250° C. and preferably about 150 to 200° C. An alkaline metal lower alkoxide is again used in catalytic quantities for the transesterification to glycerids and other esters.

After the formation of the glycerides, or other esters in the transestrification reaction are produced, the reaction medium is neutralized with an acid as in the case of the transesterification above for the formation of the lower alkyl esters of the fatty acids from lipid mixtures or phospholipids. The neutralized reaction medium is then treated to remove waste materials and recover a composition containing esters, e.g., glycerides, of the lipid source, e.g., egg yolk fatty acids, including that of AA and DHA, i.e., the Processed Natural Ingredients. Conventional techniques can be used for this purification, e.g., such as washing the neutralized reaction medium with water, after which the lipid is dried with heat, vacuum or both. The Processed Natural Ingredients will contain at least 1 wt % of AA such as about 1 wt % to 15 wt % of AA and at least 0.1 wt % of DHA such as about 0.1 wt % to 5 wt % of DHA and preferably less than 0.01 wt % of phosphorus and less than 0.5 wt % of cholesterol.

After removing wastes from and drying the glycerides, the glycerides are optionally subjected to decolorization such as by contact with activated carbon and the solids from such process then removed, e.g., by a filter press to recover the Processed Natural Ingredients which contain the glycerides of AA and DHA together with small quantities of cholesterol and even smaller quantities of phosphorus. Additionally the decolorized glycerides can be deodorized to remove all volatile components such as free fatty acids, or lower alkyl ester thereof, and residual solvent. Such processing is typical for the production of edible glyceride oils.

The Free Fatty Acid Route

In the free fatty acid route, fatty acids, fatty acid esters, and mixtures thereof high in polyunsaturated fatty acids are prepared. As in the ester route the lipids can be derived from naturally occurring lipid mixtures and the resulting acids, esters and mixtures thereof of this invention have low levels of cholesterol, sterols and phosphorus compounds which are preferably essentially free of cholesterol, sterols, and phosphorus compounds as described hereinabove. The free fatty acid route of this invention involves up to five steps. These steps are set forth above in the Disclosure of the Invention in the aspect of the free fatty acid route. The free fatty acid route starts with the same starting materials as the ester route.

In the first step, Step (A), the lipid mixture containing phospholipids, triglycerides, and sterols is hydrolyzed in water to form a two-phase product containing a fatty acid phase comprised of free fatty acids and sterols, and an aqueous phase comprised of water, glycerol, and glycerol phosphoric acid esters.

The hydrolysis of the lipid mixture in Step (A) may be catalyzed by either the addition of an acid or a base. Preferably, the hydrolysis of the lipid mixture in Step (A) is accomplished by a base-catalyzed hydrolysis reaction. Such base-catalyzed hydrolysis reactions are commonly known as saponification reactions. Suitable base catalysts are aqueous alkali which include sodium, lithium, calcium, and potassium salt of an hydroxide, carbonate or bicarbonate. Combinations of base catalysts may also be used.

The hydrolysis reaction in Step (A) is an equilibrium-limited reaction. The base-catalyzed reaction is driven to completion through the formation of a metal salt of the corresponding fatty acid. The base catalyst is added in at least a stoichiometric amount up to two times the stoichiometric amount based on the equivalents of fatty acid groups contained in the lipid mixture. Preferably, the base catalyst is added in an amount of 1.1 to 1.5 times the equivalent of fatty acid groups contained in the lipid mixture.

In a base-catalyzed hydrolysis the metal salts of fatty acids formed during hydrolysis are acidified to a pH of 4 or less with a mineral acid to form a two-phase product containing a fatty acid phase comprised of free fatty acids and sterols, and an aqueous phase comprised of water, glycerol, and glycerol phosphoric acid ester residues.

Mineral acids useful for the acidification of the metal salts of the fatty acids must have a pKa lower than the pKa of the free fatty acid. Suitable mineral acids include sulfuric acid, nitric acid, hydrochloric acid, and phosphoric acid. Combinations of mineral acids may also be used. The mineral acid is added in at least a stoichiometric amount based on the amount of base catalyst. The mineral acid may be added in dilute or concentrated form. A preferred mineral acid is aqueous hydrochloric acid.

In the absence of a suitable quantity of lower alkanol in Step (A), unreacted phospholipids and hydrolyzed phospholipid residues act as surfactant and may interfere with the formation of distinct fatty acid and aqueous phases in Step (A). In the event that the lipid mixture of Step (A) does not contain a lower alkanol in suitable quantity, a lower alkanol may be added to the hydrolysis product in Step (A) to assist in two-phase formation. The alcohol solubilizes the fatty acids and helps partition the surfactant residues into the aqueous phase. The alcohol is added at a 0.5:1 to 3:1, preferably a 1.5:1 mass ratio of alcohol to phospholipid present in the lipid mixture fed to Step (A). Examples of lower alkanols suitable to aid in two-phase formation include methanol ethanol propanol, isopropanol, isobutanol, and butanol. The addition of lower alkanol outside this range either does not result in the formation of a two phase mixture or results in poor partitioning of triglycerides and phospholipids into their respective phases.

In the second step, Step (B), the aqueous phase is separated from the fatty acid phase of the two-phase product formed in Step (A). The aqueous phase is removed by methods known in the art such as decantation. It is important to note that at acidic pH, the fatty acids may form fatty acid alcohol esters with any lower alkanol used optionally in Step (A). The fatty acid alcohol esters are undesirable as they represent a yield loss of fatty acids. Therefore, it is desirable that: (1) the two-phase product formed in Step (A) be maintained at a low temperature to slow the esterification reaction, but at a temperature which maintains the fatty acids as a liquid phase, between 35° C. to 55° C., preferably 40° C. to 50° C.; and (2) the aqueous phase should be removed as soon as practical from the two-phase product.

In the third step, Step (C), the fatty acid phase from Step (B) is heated at a temperature of 150° C. to 250° C., preferably 170° C. to 230° C., to allow the fatty acids to react with the sterols to form sterol fatty acid esters and water. Optionally water is removed from the reaction to drive the equilibrium toward the formation of the sterol fatty acid esters. The formation of fatty acid sterol esters represents a yield loss of fatty acids, including a statistical distribution of polyunsaturated fatty acids based on their percentage in the mixture, equal to one mole of fatty acid for each mole of sterol ester formed. This yield loss is necessary in order to convert the sterols into sterol esters which can be separated easily from fatty acids.

Optionally an esterification catalyst can be added in Step (C) to increase the rate of sterol fatty acid ester formation. Examples of suitable esterification catalysts include: dibutyl tin oxide, phosphoric acid, zinc oxide, hydrochloric acid, and butyl stannoic acid.

In the fourth step, Step (D), the fatty acid and sterol ester mixture formed in Step (C) is distilled at a temperature of 130° C. to 250° C. and a pressure of $1 \times 10^{-3}$ kPa to 0.5333 kPa, to recover purified fatty acids. The distillation is preferably conducted at a temperature of 180° C. to 220° C. and a pressure of $1 \times 10^{-3}$ kPa to 0.0667 kPa. The fatty acids are relatively volatile and distill overhead, while the sterol fatty acid esters are not volatile and remain with the residue. The molecular weight distribution of the fatty acid residues of subsequently derived glyceride products can be controlled by distillation. For example, the lower molecular weight fatty acids tend to be the lower boiling fatty acids and concentrate in the first fractions of the distillation; and the higher molecular weight acids are found in the higher boiling fractions. The resulting fatty acids are essentially free of sterol compounds and phosphorus containing residues. Successive distillation stages may be used to remove lighter acids and concentrate heavier polyunsaturated acids such as AA, DHA, and EPA.

The formation of sterol fatty acid esters are critical to the present invention in order to recover fatty acids in high yield which are free of sterols and sterol esters. The relative volatility between the high molecular weight polyunsaturated fatty acids such as AA, DHA, and EPA, and the sterol esters is relatively large. Thus, the polyunsaturated fatty acids can be separated sharply from the sterol esters with any single equilibrium stage, non-refluxed high vacuum distillation apparatus known in the art, including a wiped-film evaporator, a falling film evaporator, a short path evaporator, and a centrifugal molecular still.

Alternatively, the relative volatility of the free sterols and the high molecular weight polyunsaturated fatty acids such as AA, DHA, and EPA is relatively small. Thus, a sharp separation of free sterols from higher molecular weight polyunsaturated fatty acids is not practical by single equilibrium stage, non-refluxed high vacuum distillation methods.

Multistage fractional distillation devices with reflux which are capable of sharp separations between components of low relative volatility such as free sterols and fatty acids must operate at higher pressures and subsequently higher temperature in order to allow for sufficient pressure drop across the multistage column. The requisite higher temperatures required in a multistage distillation leads to undesirable heat degradation and cis-trans isomerization of the unsaturated fatty acids.

Other methods of separation of sterols such as crystallization or supercritical extraction are more difficult and expensive. The melting points of sterols and fatty acids overlap and a sharp separation requires complicated, expensive fractional crystallization equipment and refrigeration. Supercritical extraction requires expensive high pressure equipment to maintain the extractant at supercritical conditions.

Optionally, the purified fatty acids, free of sterols and phosphorus containing residues, from Step (D) may be mixed with a C1–C10 alkyl monohydric or polyhydric alcohol and heated to produce a fatty ester of the alcohol, Step (E). Suitable monohydric alcohols include, for example, methanol, ethanol, propanol, isopropanol, and butanol. Suitable polyhydric alcohols include, for example, glycerin, propylene glycol, ethylene glycol, sorbitol, sucrose, erythritol, pentaerythritol, mannitol, fructose, glucose, xylitol, and lactitol. The monohydric or polyhydric alcohol is added in a molar ratio of 1 to 2 moles of fatty acid to each hydroxyl equivalent of the alcohol, preferably, in a molar ratio of 1.1 to 1.3 moles of fatty acid to each hydroxyl equivalent of the alcohol. Optionally, water may be removed during the esterification reaction to drive the equilibrium toward the ester product.

The Processed Natural Ingredients in the free fatty acid route are obtained after separation of the glycerides from the esterification reaction as in the case of the ester route. Optionally the Processed Natural Ingredients are purified such as by deodorization and decoloration. The Processed Natural Ingredients can be the glyceride composition from the esterification reaction with glycerol or preferably such glyceride composition after purification in both the free fatty acid route and the ester route.

In both the free fatty acid route and the ester route, it is often desirable to increase the ratio of the unsaturated fatty acids or lower alkyl esters thereof in relation to the saturated fatty acids or lower alkyl esters thereof. As shown in Examples 5, 6, and 7 hereof, this can be accomplished by various fractionation techniques such as solvent fractionation, solid fractionation such as cold pressed techniques, etc. Such fractionation can rely on the melting or solidification temperatures of the egg yolk saturated fatty acids and esters thereof in relation to the unsaturated egg yolk fatty acids and esters thereof. The fractionation can be applied to the crude free fatty acids or the lower alkyl esters thereof before the distillation step or to the purified free fatty acids or lower alkyl esters thereof after distillation.

The concentration of glycerides in the Processed Natural Ingredients from either the ester route or the free acid route can vary from that of at least about 60%, preferably at least about 70% and particularly at least 85 to 90% based on the weight of the Processed Natural Ingredients composition. The remainder is generally that of various reactants, intermediate products and solvents used in the method of this invention together with the small amounts of cholesterol and phosphorus. Illustratively, such remainder can contain: alkanols and various other solvents as well as unreacted fatty acids or lower alkyl esters thereof.

A typical fatty acid profile of some of the more significant individual fatty acids of the triglycerides in the egg derived triglycerides is set forth in Table A below.

TABLE A

ANALYSIS OF EGG YOLK DERIVED TRIGLYCERIDE OF THIS INVENTION

| Fatty Acid Profile | Relative Amount Based on Total of Fatty Acids Shown |
|---|---|
| C16:0 | 29.5 |
| C18:0 | 11.0 |
| C18:1 | 40.3 |
| C18:2 | 15.6 |
| C20:4w6 (AA) | 2.9 |
| C22:6w3 (DHA) | 0.8 |
| Total | 100.1 |

| Other components of Egg Derived Triglycerides | Amount (mg/100 g) |
|---|---|
| Cholesterol | less than 50 |
| Phosphorus | less than 10 |

The enteral formula of this invention can generally be prepared using the following method. An appropriate quantity of protein is dispersed in sufficient water or oil to solubilize or suspend it, thereby forming a protein solution/suspension. Typically this protein source would be intact milk or soy proteins and/or hydrolyzed milk or soy proteins. A carbohydrate source, such as one or more of corn syrup solids, lactose, maltodextrins and sucrose is dissolved in water, thereby forming a carbohydrate solution. A source of dietary fiber, such as soy polysaccharide, may also be added. Appropriate minerals are dissolved in water, the carbohydrate solution or oil, so as to form a mineral solution.

Once formed, the three solutions (protein, carbohydrate, and mineral) are combined in appropriate quantities with oils, especially the oils obtained by the instant process and oil soluble vitamins. This resulting solution is then heat processed and homogenized. Following processing, water soluble vitamins, iron, choline and other nutrients are added and then nucleotides may be added. The solution is then diluted with water to the appropriate caloric density, approximately 670–725 kcal per liter of formula. The formula is then dispensed into containers and retorted to obtain commercial sterility or packaged aseptically using commercially available techniques and equipment. As prepared, the formula contains appropriate nutrients in compliance with the Infant Formula Act as of the date of this application. It should also be recognized that the unique formula of this invention could be prepared for use in powdered form or as a concentrated liquid.

The enteral formula can also simply comprise a nutritional source of amino nitrogen, carbohydrates, edible fats, minerals, or vitamins, together with the egg derived triglycerides of this invention. Preferably, the egg derived triglycerides will provide from about 0.1 wt % to about 2 wt % of AA and typically about 1 wt % based on the total fat in the infant formula and DHA from about 0.05 wt % to about 0.5 wt % based on the total fat in the infant formula.

An enteral formula of this invention is shown in Table B below

TABLE B

FORMULA ACCORDING TO THE INVENTION

| NUTRIENT | CONCENTRATION PER LITER OF FORMULA |
|---|---|
| Protein | 13.0–20 g |
| Protein Source | |
| Condensed Skim Milk | 55–75% |
|  | 7.15–15 g |
| Whey Protein Concentrate | 25–45% |
|  | 3.25–9 g |

TABLE B-continued

FORMULA ACCORDING TO THE INVENTION

| NUTRIENT | CONCENTRATION PER LITER OF FORMULA |
|---|---|
| Lipid | 13–40 g |
| H.O. Safflower Oil | 35–55% |
| Soy Oil | 20–40% |
| Coconut Oil | 20–45% |
| triglycerides from egg derived triglycerides | 2–20% |
| Carbohydrate Lactose | 70–110 g |
| Nucleotides | 70–100 mg |
| Cytidine monophosphate | 29–39 mg |
| Uridine monophosphate | 15–21 mg |
| Adinosine monophosphate | 10–16 mg |
| Guanosine monophosphate | 14–20 mg |
| Iron | 8–16 mg |
| R, R, R, α tocopherol | 10–30 IU |
| βCarotene | 375–575 μg |
| Selenium | 14–32 mcg |
| Calcium | 475–850 mg |
| Phosphorus | 240–700 mg |
| Ca:P Ratio | 1.4–2.4 |

Although the percentage of triglycerides from the egg derived triglycerides is 2 to 20% in the above preferred enteral formula, the quantity of the other lipids can be decreased so that the triglycerides from the egg derived triglycerides can make up about 2 to 95% of the lipids. The amount of egg derived triglycerides in the infant formula is generally less than about 36 g per liter of formula.

Also contemplated by this invention is the use of the egg-derived triglycerides in a nutritional supplement for humans and animals that may be in the form of a pill or capsule. More specifically, the nutritional supplement in accordance with this invention could be used by pregnant and/or lactating females.

The following examples are illustrative of the invention. All parts and percentages in the examples, as well as elsewhere in this application, are by weight. Room or ambient temperature is 23 degrees C., unless the context indicates otherwise.

EXAMPLE 1

Preparation of Egg Derived Triglycerides by Ester Route

Type Y-1 Egg yolk solids of Henningsen Foods, Inc. of 14334 Industrial Road, Omaha Nebr. were used in this example. Such egg yolk solids have the following chemical and physical standards: moisture of 0.5% maximum; pH of 6.5±0.3; fat of 56% minimum; protein of 30% minimum; color of 40–60 ppm Beta-carotene; and granulation so that 100% passes through U.S.S.S. # 16 screen. Egg yolk solids (455.7 g) Henningsen Foods type Y-1 were placed in a beaker (2 liters [L]) with methanol (1 L), heated to 60° C. and stirred with a magnetic stir bar. The yellow slurry was stirred for 1 hour and after a brief cooling period the solids were removed by vacuum filtration. The insoluble egg yolk components contained in the funnel were washed with an additional amount of methanol (2×200 ml). The filtrate was placed in a 3-neck round bottom flask (1 L) and a portion of the methanol was removed by distillation so that all the filtrate could by accommodated by the one liter flask. The acid content of the methanol lipid mixture was determined by titrimetric measurement and an equal number of moles of sodium methoxide was added so as to neutralize any acid. An additional amount of sodium methoxide (1 g) was added to act as catalyst for the transesterification of the egg lipids to methyl esters. After approximately one hour the reaction was complete as determined by TLC (thin layer chromatography) indicating that all of the egg lipids had been converted to methyl esters. The reaction was quenched by the addition of phosphoric acid (0.7 g). The acid addition caused the formation of a precipitate. After cooling the precipitate was removed by vacuum filtration. The filtrate separated into two phases. The upper orange layer contained mostly methyl esters and a small amount of methanol solvent. The lower dark layer contained some methyl esters and most of the methanol. The lower layer was nearly water dispersable. After removal of the excess methanol from the lower layer, an additional amount of the crude methyl esters could be isolated. The combined crude methyl esters (82.4 g) were distilled with a short path glass evaporator (UIC Inc., KDL-4 Unit) at vacuum of 0.045 mm Hg and jacket temperature of 100° C. This clear and colorless distillate (60.4 g) of purified egg derived methyl esters contained 0.46 wt % cholesterol and less than 5 ppm of phosphorus. The purified methyl esters (45 g) were combined with glycerin (4.6 g) in a 3 neck round bottom flask (100 ml). The flask was purged with nitrogen and a nitrogen atmosphere was maintained throughout. The immiscible mixture was stirred vigorously with a magnetic stir bar. After drying the mixture at elevated temperatures, sodium methoxide (0.5 g) was slowly added to the reaction mixture. Heating was maintained between 110–170° C. for 24 hours. TLC indicated that the reaction was slowly proceeding. An additional amount of sodium methoxide (0.2 g) was added and heating continued an additional 24 hours. Afterwards the reaction mixture was cooled and neutralized by the addition of 85% phosphoric acid (0.5 g). The mixture was washed with water (5×20 ml) and dried with heat and vacuum. The oil was deodorized with a short path glass evaporator to remove all volatiles including unreacted methyl esters in order to obtain the egg yolk derived triglycerides.

Table 1

This table sets forth the composition of the egg derived triglycerides prepared in Example 1. The extracted lipids from the egg powder dissolved in methanol are referred to as "Extract"; and the decolorized and deodorized triglyceride egg derived triglycerides referred to as "Purified Triglyceride". This table also shows quantities of fatty acids and cholesterol obtained in another experiment involving the method of this invention for a crude triglyceride before deodorization and decolorization which is simply referred to as "Crude Product". The quantitative results are expressed as grams in 100 grams of sample. The designation "N/D" means that the quantity was not detectable whereas "N/R means not reported.

|  | Extract | Distilled Methyl Esters | Crude Product | Purified Triglyceride |
|---|---|---|---|---|
| Cholesterol | 2.786 | 0.465 | N/D | N/D |
| Fatty acids |  |  |  |  |
| C14:0 | 0.156 | 0.347 | 0.303 | 0.310 |
| C14:1 | 0.025 | 0.066 | N/R | N/R |
| C15:0 | 0.037 | 0.080 | N/R | N/R |
| C16:0 | 13.790 | 27.051 | 24.821 | 23.371 |
| C16:1 | 1.148 | 2.586 | 2.370 | 2.250 |
| C16:2 | 0.024 | N/R | N/R | N/R |

-continued

|  | Extract | Distilled Methyl Esters | Crude Product | Purified Triglyceride |
|---|---|---|---|---|
| C16:3 | 0.080 | 0.172 | 0.162 | 0.152 |
| C16:4 | 0.073 | N/R | N/R | N/R |
| C18:0 | 5.912 | 9.925 | 9.344 | 8.725 |
| C18:1 | 18.695 | 36.121 | 34.095 | 31.969 |
| C18:2 | 7.875 | 14.203 | 13.213 | 12.361 |
| C18:3 | 0.192 | 0.331 | 0.264 | 0.248 |
| C18:4 | 0.067 | 0.058 | 0.187 | 0.176 |
| C20:0 | N/R | 0.030 | N/R | N/R |
| C20:1 | 0.123 | 0.223 | 0.210 | 0.206 |
| C20:2w6 | 0.152 | 0.157 | 0.219 | 0.224 |
| C20:3w6 | 0.178 | 0.264 | 0.243 | 0.233 |
| C20:4w6 (AA) | 2.096 | 2.882 | 2.500 | 2.367 |
| C20:5w3 | N/R | 0.032 | N/R | N/R |
| C21:5 | 0.036 | N/R | R/R | N/R |
| C22:4w6 | 0.130 | 0.141 | 0.123 | 0.123 |
| C22:5w6 | 0.493 | 0.636 | 0.453 | 0.439 |
| C22:5w3 | 0.070 | 0.083 | N/R | N/R |
| C22:6w3 (DHA) | 0.675 | 0.616 | 0.612 | 0.596 |
| TOTAL | 52.026 | 96.568 | 89.124 | 83.750 |

EXAMPLE 2

Preparation of Egg Derived Triglycerides by Ester Route

Egg yolk powder (8 batches of 500 g, or 4,000 g total) was mixed with methanol (8 batches of 1,000 ml, or 8,000 ml total) and heated to 50–60 degrees C. with stirring. The egg powder did not freely disperse in the methanol, and the clumps of egg powder had to be broken up via a spatula. The extraction time averaged about 45–60 minutes before the slurry was filtered through a Buchner funnel. The egg protein filtered very quickly, and an additional 200 ml of methanol (per batch) was used to wash the insoluble egg yolk components.

By isolation of the extract in a separate experiment, the acid value of the extract was about 12. In order to reduce the usage of sodium methoxide for the transesterification, 21.6 g of calcium oxide was added. This amount of calcium oxide was enough to neutralize an acid value of 12, assuming that the weight of the extract is 50 wt % of the egg powder. Afterward the yield of the extract from egg powder was estimated to be about 33 wt % and therefor an excess of calcium oxide was probably used.

To initiate the transesterification, 36 ml of 25% sodium methoxide in methanol was added to the methanol solution at room temperature. Within one hour, the reaction was nearly complete, but the reaction was stirred overnight for convenience. There was not a glycerol layer in the bottom of the reaction flask as would be normally expected, but there were calcium salts suspended in the mixture. Acetic acid (9.45 g ) was added to neutralize the sodium methoxide before the removal of methanol. Methanol was removed by distillation by heating the reaction mixture up to a temperature of 75 degrees C., and finally heating under vacuum.

The residue was poured into centrifuge bottles, and placed in a centrifuge set to run at 4,000 rpm for 15 minutes at room temperature. After centrifugation, there were two phases in the bottles, and the dark orange upper layer was decanted from the calcium salt residue. The calcium salt residue weighed 382 g. The orange colored upper layer was not totally homogeneous, and it appears that cholesterol was crystallizing out.

The orange colored decantate was diluted with about 275 g of triglyceride oil previously isolated from the egg yolk phospholipids. This nonvolatile triglyceride oil was added to lubricate the rotors of the Pope still because of the high cholesterol concentration of the decantate. The decantate was added to the still. At a vacuum of 1 mm Hg, the distillation was conducted at a temperature of 200±20 degrees C. This temperature is the set point of an external heating mantle on the Pope still, and this is not the temperature where the methyl esters actually distill.

From this distillation was obtained, 820 g of distilled methyl esters. These methyl esters contained 0.3% cholesterol by GC (gas chromatography) assay, and the distillate turned into a semi-solid upon standing. The residue weighed 489 g. From these isolated yields, one obtains the following:

|  |  |
|---|---|
| Calcium salt residue | 382 grams |
| distilled methyl esters | 820 grams |
| distillation residue | 489 grams |
| triglyceride diluent | −275 grams |
| calcium oxide added | −21 grams |
| sodium methoxide | −10 grams |
| acetic acid | −10 grams |
| Total isolated weight | 1375 grams |

This isolated weight shows that the extract weight was about 30 wt % based on egg powder.

About 741 grams of the distilled methyl esters was used for the final esterification. This distillate was mixed with 82 g of glycerol and 10 ml of 25% sodium methoxide. The esterification reaction started at 75° C., and was gradually increased. The temperature was started this low because analogous esterifications with methyl oleate began to darken at this temperature. No darkening of the reaction mixture occurred up to 150 degrees C. The temperature was later increased to 170 degrees before the reaction was terminated. After 7 days of constant heating, there was no sign of major decomposition, and the product color was very light. The reaction mixture was cooled to 75 degrees and 4.5 g of 85% phosphoric acid was added to neutralize the sodium methoxide catalyst, and then hot water (400 ml) was added to wash away the acid salts. Two additional hot water washes were used to remove the salts. Hot water was necessary to reduce the formation of emulsions. The product was then heated to 95 degrees C. under vacuum to degas and dry the sample. This product, referred to herein as the egg derived triglycerides weighed 711 g, but this number is not an accurate yield because much of the reaction mixture was removed during sampling to analyze the progress of the reaction.

A small portion of the final product above was removed and heated to liquify the methyl esters. The sample was treated with activated carbon, and later filtered through a bed of Celite in order to decolorize it. There was a slight improvement in the color by carbon treatment.

About 120 grams of decolorized product was added to the molecular still to remove the unreacted methyl esters in order to deodorize the product. After deodorization, 87.6 g of triglyceride residue and 12.6 g of methyl ester was isolated. The lost 20 grams is not indicative of the process, and it is only the holdup and loss after small scale distillation. However, the lost 20 grams is mostly methyl ester. Analysis of the product obtained by the process of this Example 2 showed the presence of AA and DHA in a higher than expected amount. The methyl ester product was remarkably stable and there was no apparent decomposition or darkening during the glycerol esterification reaction. The decolorized and deodorized triglycerides appeared to have darkened slightly during the distillation. Decoloration may not be necessary, but it appears that if performed that it be done last.

Table 2 below shows the fatty acid content of various compositions from Example 2 as a percent of total fatty acid as obtained by analyzing the fatty acid methyl esters (FAME) of the various compositions indicated in the table.

TABLE 2

| FAME | Final product Triglycerides | Distilled Esters | Starting Material Egg Powder Extract |
|---|---|---|---|
| 14:0 | 0.14 | 0.11 | 0.31 |
| 16:0 | 22.35 | 20.90 | 27.63 |
| 16:1 | 1.84 | 1.71 | 0.53 |
| 16:3 | 0.16 | 0.16 | 0.15 |
| 16:4 | N/R | N/R | 0.15 |
| 17:0 | 0.22 | 0.22 | 0.22 |
| 18:0 | 11.76 | 11.90 | 11.25 |
| 18:1 | 40.09 | 40.32 | 36.75 |
| 18:2 | 15.42 | 15.35 | 15.10 |
| 18:3w6 | 0.12 | 0.12 | N/R |
| 18:3w3 | 0.29 | 0.29 | 0.26 |
| 18:4 | 0.18 | 0.18 | 0.14 |
| 20:1 | 0.32 | 0.37 | 0.24 |
| 20:2 | 0.29 | 0.38 | 0.27 |
| 20:3 | 0.32 | 0.41 | 0.29 |
| 20:4w6 (AA) | 3.85 | 4.23 | 3.92 |
| 22:0 | N/R | 0.13 | 0.14 |
| 22:4 | 0.26 | 0.35 | 0.24 |
| 22:5w6 | 1.02 | 1.18 | 0.98 |
| 22:5w3 | 0.11 | 0.21 | 0.15 |
| 22:6w3 (DHA) | 1.27 | 1.47 | 1.26 |
| Total | 100.00 | 100.00 | 100.00 |

EXAMPLE 3

Egg Powder Extraction of Lipid with Various Solvents

| Solvent | Temperature | Yield % (fat) | % AA |
|---|---|---|---|
| 2:1 CHCl$_3$/CH$_3$OH | 50–60° C. | 64.2 | 2.0 |
| Isopropyl alcohol | 50–60° C. | 60.0 | 1.8 |
| Methyl alcohol | 50–60° C. | 37.3 | 4.2 |
| Ethyl alcohol | 50–60° C. | 57.2 | 2.2 |
| Ethyl alcohol | 22° C. | 41.1 | 2.7 |
| Ethyl alcohol | 4° C. | 25.2 | 3.7 |

The above extractions were performed similarly to the extraction described in Example 1. It can be seen from the above table that mixture of trichloromethane and methanol gave a high yield of total fat but the AA was only 2.0% in the fat. The methyl alcohol gave a relatively low yield of total fat but a very high yield of AA in the fat. The isopropyl alcohol as well as the two runs of ethyl alcohol at 50–60 and 22° C. give relatively high yields of total fat but small yields of AA in the fat. The ethyl alcohol at 4 degrees C. gave the smallest yield of total fat but a relatively high yield of AA in the fat. It can be seen from the above that at temperatures above about 20 degrees C., the methanol was superior compared to the other solvents in the percentage of AA extracted in the lipids. At 4 degrees C. the percentage yield of AA in the fat had increased for ethanol but the yield was lower at that temperature for ethanol as to total fat and AA in comparison to the methanol.

EXAMPLE 4

Solvent Fractionation of Distilled Fatty Acids

A sample of distilled egg derived fatty acids (1 g) was dissolved at room temperature in hexane (4 ml). The sample was placed in the refrigerator at a temperature of approximately 5 degrees C. After cooling for two days a white solid had precipitated. A portion of the clear supernatant liquid was isolated and an FAP (fatty acid profile) was obtained. The results are shown below wherein FAME means fatty acid methyl ester; S.M. means starting material, namely, the distilled egg derived fatty acids; and Prod. means the clear supernatant liquid. The acids are merely designated by the number of carbon atoms of the acid and the number of unsaturated groups (after the colon) for the particular acid involved.

| FAME | S. M. | Prod. |
|---|---|---|
| C16:0 | 22.7 | 13.5 |
| C18:0 | 11.6 | 5.2 |
| C18:1 | 40.0 | 47.7 |
| C18:2 | 15.3 | 18.8 |
| C20:4 | 3.8 | 4.9 |
| C22:6 | 1.2 | 1.4 |

From the results of the above Example 4 it can be seen that the solvent fractionation of the distilled fatty acids increased the concentration of the unsaturated fatty acids. The solid precipitate appears to be mostly saturated fatty acids. Thus, this procedure increases the concentration of unsaturated fatty acids such as AA and DHA which in turn reduces the amount of egg derived triglycerides needed in an enteral formula to achieve desired levels of AA and DHA.

EXAMPLE 5

Solvent Fractionation of Methyl Esters

A sample of egg yolk methyl esters extracted with methanol from egg yolk prior to distillation to remove cholesterol was dissolved in hexane (4 ml). The sample was placed in the freezer at a temperature of approximately −20 degrees C. After cooling for two days a solid precipitate formed. A portion of the supernatant liquid was isolated and an FAP was obtained. The abbreviations in the below table are the same as those of Example 4 above and again it can be seen that the fractionation increased the concentration of unsaturated fatty acids such as AA and DHA.

| FAME | S. M. | Prod. |
|---|---|---|
| C16:0 | 26.7 | 14.7 |
| C18:0 | 11.6 | 4.2 |
| C18:1 | 36.4 | 46.6 |
| C18:2 | 13.6 | 17.4 |
| C20:4 | 3.7 | 4.8 |
| C22:6 | 0.9 | 1.1 |

EXAMPLE 6

Cold Temperature Fractionation of Methyl Esters

A sample of distilled egg yolk derived methyl esters (1 g) was placed in a syringe (5 ml.) in which the end was plugged with a small piece of cotton. The plunger of the syringe was inserted and all air was removed from the syringe body. The syringe, containing the sample, was placed in the refrigerator at a temperature of approximately 5° C. After cooling for two days the entire syringe contents appeared to be a solid white mass. The syringe was removed from the refrigerator and pressure was quickly applied to the plunger and a clear liquid fraction was isolated. An FAP of the clear liquid was obtained. The results are shown below wherein the meaning of abbreviations is the same as in Example 4 and again it can be seen that this procedure increases the concentration of unsaturated fatty acids such as AA and DHA.

| FAME | S. M. | Prod. |
|---|---|---|
| C16:0 | 27.8 | 14.4 |
| C18:0 | 10.5 | 4.6 |
| C18:1 | 36.1 | 47.3 |
| C18:2 | 14.6 | 19.0 |
| C20:4 | 3.1 | 4.0 |
| C22:6 | 0.8 | 1.0 |

EXAMPLE 7

Liquid egg yolk (292.5 g; "Easy Eggs", M. G. Waldbaum, Gaylord Minn.) was mixed with ethanol (690 ml) in a one liter beaker and stirred with a magnetic stir bar. The mixture was heated with a hot plate until boiling. Boiling was continued for 10 minutes. The mixture was cooled for several minutes and then filtered with a buchner apparatus. The insoluble egg yolk components were first rinsed with ethanol (100 ml) and then removed from the funnel and stirred in an additional amount of ethanol (250 ml) at room temperature for 5 minutes. The solid material was again filtered and washed with ethanol (100 ml). The combined ethanol solutions were placed in single separatory funnel and allowed to stand undisturbed over night. A phase separation occurred and the lower layer, mostly triglyceride, was removed. The ethanolic solution of egg phospholipids was placed in a 3-neck round bottom flask (1 L). Sodium hydroxide pellets (2.56 g) were added to the mechanically stirred solution. Heating commenced and ethanol was removed by simple distillation. After approximately 250 ml of ethanol had been removed by distillation, TLC indicated that the reaction mixture contained a significant amount of ethyl esters. An additional amount of sodium hydroxide pellets (1.5 g ) were added and ethanol distillation continued. After another 125 ml of ethanol was removed, TLC indicated that the reaction mixture contained no ethyl ester and only fatty acids of the original egg phospholipid extract. Heat was removed from the flask and after cooling several minutes, concentrated HCl (6 ml) was added to the mixture in order to neutralize the base. Water was added to the cooled mixture and then the entire solution was extracted with hexane (2×400 ml). The combined hexane extracts were dried with sodium sulfate and the hexane was removed under reduced pressure. A dark orangish oil (14.65 g ) was obtained. The oil was again dissolved in hexane (50 ml) and placed in a refrigerator at a temperature of 0–5° C. and allowed to stand overnight. A solid fraction precipitated from the hexane solution and was isolated by filtration. The hexane filtrate was placed in the freezer (–20° C.)and allowed to stand for 6 hours. Again, a solid precipitate formed that was isolated by filtration. The filtrate was stripped of solvent under reduced pressure to yield a dark orange oil (6.68 g). GC analysis of the various fractions indicates that the solid materials are principally saturated free fatty acids and the liquid fractions show increasing concentrations of unsaturated fatty acids. Tables 7A and 7B below show the relative fatty acid profile of various samples of this example wherein:

Sample A, also referred to as Folch Ext. is the Folch extract of liquid egg yolks;

Sample B, also referred to as EtOH Trigl., is the triglyceride fraction isolated from ethanol extract;

Sample C, also referred to as EtOH Acids, is the first fraction of crude fatty acids (no cold/solvent fractionation)

Sample D, also referred to as 0 C. Liq. Frac., is the liquid fraction from 0–5° C. hexane fractionation;

Sample E, also referred to a –20° C. Liq. Frac., is the liquid fraction from –20° C. hexane fractionation;

Sample F, also referred to as 0 C. Solid Frac., is the solid precipitate fraction from 0–5° C. hexane fractionation; and Sample G, also referred to as –20 C. Solid Frac., is the solid precipitate fraction from –20° C. hexane fractionation.

The free fatty acids, as prepared above prior to extraction with hexane, can then be distilled to separate such acids from cholesterol, preferably after heating to form cholesterol esters with the free fatty acids. The distillate of purified free fatty acids can then be subjected to esterification with glycerol to prepare the egg derived triglyceride of this invention.

TABLE 7A

| | Relative FAP | | | |
|---|---|---|---|---|
| FAME | Sample A Folch Ext. | Sample B EtOH Trigl. | Sample C EtOH Acids | Sample D 0 C. Liq. Frac. |
| C16 | 26.71 | 25.95 | 28.76 | 22.04 |
| C16:1 | 2.90 | 3.42 | 1.54 | 1.80 |
| C18 | 8.89 | 7.67 | 12.46 | 8.68 |
| C18:1 | 41.31 | 45.19 | 29.72 | 34.88 |
| C18:2 | 14.45 | 14.10 | 16.04 | 18.83 |
| C20:4w6 | 2.10 | 1.03 | 6.27 | 7.44 |
| C20:5W6 | 0.52 | 0.22 | 1.73 | 2.06 |
| C22:6w3 | 0.47 | 0.20 | 1.70 | 2.02 |
| Total | 97.35 | 97.78 | 99.22 | 97.75 |
| AA/DHA | 4.47 | 5.15 | 3.69 | 3.68 |

TABLE 7B

| | Relative FAP | | |
|---|---|---|---|
| FAME | Sample E –20 C. Liq. Frac. | Sample F 0 C. Solid Frac. | Sample G –20 C. Solid Frac. |
| C16 | 6.24 | 54.97 | 58.68 |
| C16:1 | 2.42 | 0.00 | 0.37 |
| C18 | 1.87 | 32.39 | 27.59 |
| C18:1 | 46.62 | 7.13 | 7.09 |
| C18:2 | 25.41 | 4.00 | 3.55 |
| C20:4w6 | 9.96 | 1.50 | 1.31 |
| 20:5w6 | 2.75 | 0.00 | 0.35 |
| 22:6w3 | 2.68 | 0.00 | 0.33 |
| Total | 97.95 | 99.99 | 99.27 |
| AA/DHA | 3.72 | N/AP | 3.97 |

It can be seen from Table 7B that fractional crystallization of fatty acids in hexane increases the concentration of the unsaturated fatty acids while dramatically reducing the amount of saturated fatty acids.

EXAMPLE 8

Preparation of Triglycerides by Free Fatty Acid Route

A 500 mL three neck flask equipped with a mechanical stirrer, reflux condenser, addition funnel, thermowell, heating mantle, and nitrogen atmosphere was charged with 154 grams of lipid mixture, obtained by the leaching of powdered egg yolk with methanol, 193 grams of methanol, and 28 grams of water. Sodium hydroxide (80 g of 50% dilution) was added through the addition funnel. The resulting mixture was heated at 64° C. for 145 minutes. Hydrochloric acid (84 mL of 12 N) was added over five minutes. An additional 14 mL of HCl was added in small portions until a pH of 2 was attained. Stirring was stopped and the phases were allowed to separate. The aqueous (bottom) phase was separated and contained 0.58% phosphorus. The organic phase weighed 128 g and contained 6% monoglycerides, 2% fatty acid methyl esters, 5% cholesterol, and free fatty acids.

The free fatty acids, 124 g, were charged to a 300 mL 3 neck flask equipped with a mechanical stirrer, water trap, thermowell, heating mantle, and a sparge tube. The mixture was heated at 170° C. for 4 hours with a nitrogen sparge of 100 mL/min. Residual methanol, 14 g, and water of reaction were collected, the resulting product was distilled at 245° C. and 0.5 Torr (0.0667 kPa) on a wiped film evaporator to give 83 g of distillate and 16 g residue. The distillate (fatty acids) contained 0.13% cholesterol and no detectable phosphorus. The residue contained predominantly cholesterol esters of fatty acids.

A sample of the distillate fatty acids, 67 g, was charged to a 300 mL 3 neck flask equipped with a mechanical stirrer, water trap, thermowell, heating mantle, reflux condenser, and sparge tube. The sample was warmed to 110° C., and 6.6 g of glycerin was added under nitrogen. The temperature was increased to 160° C. The resulting mixture was heated for 29 hours with a nitrogen sparge of 100 mL/min. The resulting product was passed through a wiped film evaporator at 0.4 Torr and 220° C. to remove excess fatty acids. The fatty acid distillate weighed 8 g, and the triglyceride residue weighed 50 g. Analysis of the triglycerides showed 96% triglycerides and 4% diglycerides. Total cholesterol was less than 0.13%.

EXAMPLE 9

Preparation of Triglycerides by Free Fatty Acid Route

A 22 L reaction vessel was charged with 7733 grams (g) of the methanol containing phase obtained from leaching 5 kg of powdered egg yolk with 9 L of methanol at 60° C. for 3 hours. The mixture was heated to reflux and 5.7 L of methanol was distilled off. To the resulting mixture was added 2.5 L of water, followed by 750 g of 50% NaOH solution. The resulting mixture was heated at reflux (65–70° C.) with stirring for 2.5 hours. The heat was removed, and 785 mL of concentrated HCl was slowly added while the temperature of the mixture was maintained above 50° C. Agitation was discontinued, and the phases were allowed to separate. The bottom phase was separated and weighed 5764 g and contained 0.31% phosphorus. The fatty acid phase weighed 1350 g and contained 5.2% cholesterol, 0.17% phosphorus, and 5.5% fatty acid methyl esters. The fatty acid phase was charged to a 3 L flask equipped with a N2 (nitrogen gas) sparge and water trap and was heated to 170° C. for 7 hours with a sparge rate of about 1 L/min. A total of 83 g of methanol/water mixture was collected during this time. The product weighed 1216 grams and contained 0.02% cholesterol.

The product was purified by distillation through a wiped film evaporator. Distillation at 180° C. and 0.5 Torr gave 215 g of distillate that contained 13% fatty acid methyl esters, 41% palmitic acid, and 24% oleic acid. The residue was redistilled at 280° C. to give 745 g of distillate and 151 g of residue. The residue contained mainly cholesterol esters. The distillate contained the larger fraction of higher molecular weight fatty acids than the crude material.

A 2 L flask equipped with a N2 sparge and water trap was charged with 708 g of the distillate obtained at 280° C. and with 71 g of glycerin. The resulting mixture was heated at 160° C. for 24 hours. The resulting product was transferred to the wiped film evaporator and distilled at 280° C. and 0.5 Torr to give 155 g fatty acid distillate and 480 g of triglyceride product. The triglyceride product contained 90% triglycerides and 9% diglycerides.

EXAMPLE 10

Preparation of Glycerides by Free Fatty Acid Route

A 300 ml flask equipped with a mechanical stirrer, water trap, and N2 sparge was charged with 80.5 g of fatty acid distillate recovered from Example 9, and with 7.82 g of glycerin. The resulting mixture was heated at 230° C. with a N2 sparge for 3 hours. The mixture contained 86% triglycerides and 12% diglycerides.

EXAMPLE 11

Preparation of Fatty Acids by Free Fatty Acid Route

The procedure descried in Example 9 was followed except the methanol was not distilled from the saponification step until after the NaOH was added. A 6060 g methanol solution of lipid mixture was mixed with 750 g of 50% NaOH. The resulting mixture was heated at reflux while 2 L of methanol was distilled from the mixture for 150 minutes. Water, 200 mL, was added back to the mixture and heating was continued an additional 30 minutes. The mixture was acidified to pH of 2 and was allowed to cool to 60° C. over a two hour period and the phases were separated. The fatty acid phase weighed 771 g and contained 20% fatty acid methyl esters.

EXAMPLE 12

Phase Separation of Fatty Acids in Free Fatty Acid Route

A 500 ml flask was charged with 83 g of an egg lipid mixture free of methanol, 122 ml of water, and 39 g of 50% NaOH solution. The resulting mixture was heated at 70° C. for 3 hours. Concentrated HCl (41 mL) was added over five minutes, causing a slight exotherm. The addition of HCl caused the product to form as a sticky, solid phase which could not be cleanly separated from the aqueous phase. Methanol, 122 g, was added to the mixture at 60° C. while stirring. The resulting mixture was transferred to a warm separatory funnel and the phases were allowed to separate. The aqueous phase weighed 343 g and the fatty acid phase weighed 65.6 g. The fatty acid product contained less than 2% fatty acid methyl esters.

EXAMPLE 13

Separation of Cholesterol Esters in Free Fatty Acid Route

A 1213 g sample of fatty acids that had been treated to esterify cholesterol was charged to a steam jacketed addition funnel. The material was fed to a Rodney-Hunt wiped film molecular still at a rate of 5 mL/min. The temperature of the still was maintained at 150° C. and the pressure was 0.5 Torr. A total of 215 grams of distillate was collected. The distillate contained 41% palmitic acid, 24% oleic acid, 13% fatty acid methyl esters, and less than 0.5% of C20 fatty acids. The residue was charged to the addition funnel and fed to the molecular still at a rate of 3.5 mL/min while the temperature of the still was maintained at 230° C. and the pressure was 0.4 Torr.

The distillate weighed 547 g and contained 45% oleic acid, less than 1% fatty acid methyl esters, and greater than 3% of C20 and heavier fatty acids. The residue from this fraction was charged to the addition funnel and fed to the molecular still at a rate of 3.5 mL/min while the temperature was maintained at 250° C. and the pressure was 0.35 Torr. The distillate weighed 193 g and contained 47% oleic acid, no fatty acid methyl esters, and greater than 4% of C20 and heavier fatty acids. The residue weighed 151 g and contained mainly fatty acid sterol esters and less than 2% free fatty acids.

EXAMPLE 14

Extraction of Lipids with Methanol and Phase Separation of Triglycerides From Lipids A 1,000 gal glass-lined reactor equipped with a mechanical agitator, condenser, nitrogen, and vacuum system was charged with 1,000 lb of egg yolk powder and 300 gal of methanol. The resulting mixture was heated to 65° C. and agitated for three hours. After filtering off the protein residue and washing with methanol, the methanol-lipid filtrate was returned to the 1,000 gal reactor and heated with agitation to 45° C. The agitation was stopped and the mixture was allowed to settle for one hour, with the temperature maintained between 40–45° C. Phase separation spontaneously occurred. The bottom phase was decanted off, sampled, and weighed. Analysis showed the bottom phase to weigh 96 lb and contained 94.9% triglyceride, 509 ppm phosphorus, and a fatty acid distribution on a relative basis of 0.6% arachidonic acid and 0% DHA. The top phase, upon stripping off methanol, weighed 245 lbs, and contained 4% triglycerides, 3.63% phosphorus, and a fatty acid distribution on a relative basis of 6.5% arachidonic acid and 2.0% DHA.

The Processed Natural Ingredients of this invention have utility in enteral formulas, nutritional supplements, parenteral formulas, and can serve as starting materials for various edible emulsifiers such as diacetyltartaric acid esters of mono-and diglycerides (DHTEM), succinylated mono- and diglycerides, and acylated mono- and diglycerides. The free fatty acids or lower alkyl esters of the fatty acids prepared from the egg yolk lipids can also serve as starting materials for the preparation of various other edible lipid ingredients such as polyglycerol esters, propylene glycol esters, sorbate esters, and the like.

Many variations will suggest themselves to those skilled in this art in light of the above detailed description. All such obvious modifications are within the full intended scope of the appended claims.

What is claimed is:

1. An enteral formula, said formula comprising:
(A) protein, said protein being of a concentration of between 10 and 35 grams per liter of formula;
(B) carbohydrates, said carbohydrates including those from total dietary fiber being of a concentration of between 60 and 110 grams per liter of formula; and
(C) fat, said fat being of a concentration of between 20 to 45 grams per liter of formula wherein the fat includes a triglyceride-containing ingredient derived from egg, wherein the triglycerides have ester moieties in sufficient quantity to provide, by weight based on fat in the formula, from about 0.05% to 0.5% of docosahexaenoic acid (DHA) and about 0.1% to 2% of arachidonic acid (AA) and wherein said ingredient derived from egg contains less than about 0.1% of phosphorus and less than about 5.0% of cholesterol by weight.

2. The enteral formula of claim 1, wherein the levels of protein, carbohydrate and fat are suitable for infant formula and further comprising vitamins and minerals.

3. The formula of claim 1 wherein the AA content in the triglycerides of the ingredient derived from egg is from about 1% to 15% based on the weight of said ingredient.

4. The formula of claim 3 wherein the DHA content in the triglycerides of the ingredient derived from egg is from 0.1% to 5% based on the weight of said ingredient.

5. The formula of claim 1 wherein the DHA content in the triglycerides of the ingredient derived from egg is from 0.1% to 5% based on the weight of said ingredient.

6. The enteral formula of claim 1 wherein said ingredient derived from egg is prepared by reacting glycerol with purified lower alkyl esters of fatty acids obtained by transesterifying fatty acids from egg phospholipids to obtain lower alkyl esters of the fatty acids associated with phosphorus compounds and cholesterol; and purifying the lower alkyl esters of the fatty acids by removing phosphorus compounds by phase separation in the presence of a lower alkanol; and removing cholesterol by distillation.

7. The formula of claim 6 wherein the DHA content in the triglycerides of the ingredient derived from egg is from 0.1% to 5% based on the weight of said ingredient.

8. The formula of claim 7 wherein the AA content in the triglycerides of the ingredient derived from egg is from about 1% to 15% based on the weight of said ingredient.

9. An enteral formula comprising a source of amino nitrogen, a source of carbohydrate and a source of edible fats, wherein said edible fats include a triglyceride-containing composition derived from a complex lipid mixture including phospholipids, triglycerides and sterols, and wherein said composition is prepared by the steps of:

(A) subjecting a lipid mixture containing, phospholipids, triglycerides and sterols to alkaline transesterification with a lower alkanol to form a two phase product containing a lower alkyl fatty acid ester phase comprised of lower alkyl fatty acid esters and sterols and an aqueous phase comprised of water, glycerol and phosphorus compounds;

(B) separating the aqueous phase from the lower alkyl fatty acid ester phase formed in Step (A);

(C) distilling the lower alkyl fatty acid esters and sterols from the lower alkyl fatty acid ester phase of Step (B) at a temperature of at least about 100° C. to separate and recover in the distillate lower alkyl esters of the fatty acids wherein said esters have reduced concentration of cholesterol and other sterols, and phosphorus compounds in relation to the lipid mixture of Step (A); and (D) subjecting the distilled lower alkyl esters of the fatty acids from Step (C) to transesterification in the presence of glycerol to produce fatty acid triglyceride esters.

10. The enteral formula of claim 9 wherein the lower alkanol of step (A) is methanol.

11. The enteral formula of claim 9 wherein the triglyceride composition provides from about 0.1 to about 2% of AA and from about 0.05% to about 0.5% of DHA, based on the total edible fats in the formula, and wherein the said triglyceride composition contains less than about 0.1% of phosphorus and less than about 0.5% of cholesterol based on the weight of the said triglyceride composition.

12. The formula of claim 11 wherein the lipid mixture is that from the egg yolk of hens.

13. The formula of claim 9, wherein said source of amino nitrogen is protein at a concentration of between 10 and 35 grams per liter of formula; said source of carbohydrate, including those from total dietary fiber, are at a concentration of between 60 and 110 grams per liter of formula; and said edible fats are at a concentration of between 20 to 45 grams per liter.

14. The formula of claim 13, further comprising vitamins and minerals.

15. The enteral formula of claim 9 wherein the complex lipid mixture is from hens eggs and wherein the triglyceride-containing composition is an ingredient derived from egg yolks.

16. The formula of claim 15 wherein the AA content in the triglycerides of the ingredient derived from egg is from about 1% to 15% based on the weight of said ingredient.

17. The formula of claim 16 wherein the DHA content in the triglycerides of the ingredient derived from egg is from 0.1% to 5% based on the weight of said ingredient.

18. The formula of claim 15 wherein the DHA content in the triglycerides of the ingredient derived from egg is from 0.1% to 5% based on the weight of said ingredient.

19. An enteral formula which comprises a nutritionally adequate source of amino nitrogen, carbohydrates, and edible fats, the improvement comprising the inclusion in said formula of a triglyceride composition obtained from egg yolk, said triglyceride composition being in an amount sufficient to provide from about 0.1 to 2% of AA and about 0.05% to 0.5% of DHA, based on the weight of total edible fats in the formula, and wherein the triglyceride composition contains less than about 0.1% of phosphorus and less than about 0.5% of cholesterol based on the weight of said triglyceride composition, wherein said composition is obtained by the process of:

(A) extracting lipids containing sterols, triglycerides, and phospholipids from egg yolks with methyl alcohol to obtain a solution of lipids in methyl alcohol;

(B) separating insoluble egg yolk components from the lipids in solution;

(C) forming an alkaline reaction medium of the lipids together with a catalytic quantity of an alkaline metal lower alkoxide in the solution to transesterify fatty acid glycerides of the lipids to the methyl esters of said fatty acids to produce a two phase product containing an ester phase comprised of esters and sterols and aqueous phase comprised of water, glycerol and glycerol phosphoric acid esters;

(D) separating the aqueous phase from sterols and methyl esters of said fatty acids;

(E) distilling the methyl esters of said fatty acids from sterols to recover said esters in the distillate;

(F) subjecting the distilled esters to transesterification to form a composition containing triglycerides having ester groups of said egg yolk fatty acids including AA and DHA.

20. A nutritional supplement comprising excipients and a triglyceride-containing ingredient derived from egg, wherein the triglycerides have ester moieties in sufficient quantity to provide, based on the weight of said ingredient, from about 0.1% to about 5% of docosahexaenoic acid (DHA); and wherein said ingredient contains, by weight, less than about 0.1% of phosphorus; and less than about 5.0% of cholesterol.

21. The nutritional supplement of claim 20, wherein said ingredient derived from egg further comprises about 1% to about 15% arachidonic acid (AA) based on the weight of said ingredient.

22. The nutritional supplement of claim 21 wherein the DHA content in the triglycerides of the ingredient derived from egg is from 0.1% to 5% based on the weight of said ingredient.

23. The nutritional supplement of claim 20 wherein the DHA content in the triglycerides of the ingredient derived from egg is from 0.1% to 5% based on the weight of said ingredient.

24. A nutritional supplement comprising a triglyceride composition wherein said triglyceride composition contains less than 1.0% phosphorus and less than about 5.0% of cholesterol based on the weight of the said triglyceride composition, and wherein said composition is obtained by the process of:

(A) subjecting a lipid mixture containing phospholipids, triglycerides and sterols to alkaline transesterification with a lower alkanol to form a two phase product containing a lower alkyl fatty acid ester phase comprised of lower alkyl fatty acid esters and sterols and an aqueous phase comprised of water, glycerol and phosphorus compounds;

(B) separating the aqueous phase from the lower alkyl fatty acid ester phase formed in Step (A);

(C) distilling the lower alkyl fatty acid esters and sterols from the lower alkyl fatty acid ester phase of Step (B) at a temperature of at least about 100° C. to separate and recover in the distillate lower alkyl esters of the fatty acids; and (D) subjecting the lower alkyl esters from Step (C) to transesterification in the presence of glycerol to produce a composition containing triglycerides of the fatty acid moiety of the lower alkyl esters.

* * * * *